(12) United States Patent
Blanchard et al.

(10) Patent No.: US 12,385,071 B2
(45) Date of Patent: Aug. 12, 2025

(54) METHODS FOR THE PRODUCTION OF FERULIC ACID

(71) Applicant: INVENTURE RENEWABLES, INC., Tuscaloosa, AL (US)

(72) Inventors: Cory O'Neil Blanchard, Birmingham, AL (US); William Rusty Sutterlin, Tuscaloosa, AL (US); Ryan Alexander Long, Northport, AL (US)

(73) Assignee: INVENTURE RENEWABLES, INC., Tuscaloosa, AL (US)

( * ) Notice: Subject to any disclaimer, the term of this patent is extended or adjusted under 35 U.S.C. 154(b) by 482 days.

(21) Appl. No.: 17/790,404

(22) PCT Filed: Dec. 31, 2020

(86) PCT No.: PCT/US2020/067650
§ 371 (c)(1),
(2) Date: Jun. 30, 2022

(87) PCT Pub. No.: WO2021/138549
PCT Pub. Date: Jul. 8, 2021

(65) Prior Publication Data
US 2023/0027119 A1    Jan. 26, 2023

Related U.S. Application Data

(60) Provisional application No. 62/955,917, filed on Dec. 31, 2019.

(51) Int. Cl.
*C12P 7/42* (2006.01)
*C07C 51/47* (2006.01)
*C12N 9/18* (2006.01)

(52) U.S. Cl.
CPC .............. *C12P 7/42* (2013.01); *C07C 51/47* (2013.01); *C12N 9/18* (2013.01); *C12Y 301/01013* (2013.01)

(58) Field of Classification Search
CPC .................................... C12N 9/18; C12P 7/42
See application file for complete search history.

(56) References Cited

U.S. PATENT DOCUMENTS

| 5,288,902 A | 2/1994 | Taniguchi et al. |
| 2003/0167511 A1 | 9/2003 | Narbad et al. |
| 2016/0145183 A1 | 5/2016 | Revelant et al. |
| 2019/0077741 A1 | 3/2019 | Lee et al. |
| 2023/0027119 A1* | 1/2023 | Blanchard ............. C07C 51/412 |

FOREIGN PATENT DOCUMENTS

WO    2008116319 A1    10/2008

\* cited by examiner

*Primary Examiner* — Tekchand Saidha
(74) *Attorney, Agent, or Firm* — Gregory P. Einhorn; Greer, Burns & Crain, Ltd.

(57) ABSTRACT

Provided are methods or processes for producing ferulic acid from a plant material, for example, a rice bran or its derivatives. Provided are methods comprising an ion swapping and solvent extraction process followed by a chromatographic separation operations that are coupled into a process which functions to recover a fraction rich in gamma-oryzanol, thus enabling the subsequent production of a high purity ferulic acid. Provided are methods comprising an ion swapping and solvent extraction process followed by a process which functions to recover a fraction rich in gamma-oryzanol, or a mixture of ferulic acid esters of phytosterols and triterpenoids, optionally comprising cycloartenyl ferulate, 24-methylenecycloartanyl ferulate, and/or campesteryl ferulate, to enable the production of a high purity ferulic acid. Provided are methods comprising a saponification and solvent extraction process followed by recovering a fraction rich in gamma-oryzanol to enable the production of a high purity ferulic acid.

40 Claims, 3 Drawing Sheets

NATURAL PROCESS FOR PRODUCTION OF BIO-BASED VANILLIN FROM ORYZANOL-CONTAINING FEEDSTOCK

METHODS FOR THE PRODUCTION OF FERULIC ACID

RELATED APPLICATIONS

This U.S. National Phase Patent Application claims benefit of priority under 35 U.S.C. § 371 to Patent Convention Treaty (PCT) International Application PCT/US2020/067650, filed Dec. 31, 2020, now pending, which claims the benefit of priority under 35 U.S.C. § 119(e) of U.S. Provisional Application Ser. No. 62/955,917, Dec. 31, 2019. The aforementioned applications are expressly incorporated herein by reference in their entirety and for all purposes. All publications, patents, patent applications cited herein are hereby expressly incorporated by reference for all purposes.

TECHNICAL FIELD

This invention generally relates to the extraction of lipids from plant biomass and their conversion to useful chemicals such as ferulic acid, or (2E)-3-(4-hydroxy-3-methoxyphenyl)prop-2-enoic acid. In alternative embodiments, provided are methods for producing ferulic acid from a plant material, for example, a rice bran or rice barn oil and their derivatives. In alternative embodiments, methods as provided herein comprise an ion swapping and solvent extraction process followed by a plurality of chromatographic separation operations that are coupled into a process which functions to recover a fraction rich in gamma-oryzanol (or γ-oryzanol), or a mixture of ferulic acid esters of phytosterols and triterpenoids optionally comprising cycloartenyl ferulate, 24-methylenecycloartanyl ferulate, and/or campesteryl ferulate, thus enabling the subsequent production of a high purity ferulic acid. In alternative embodiments, methods as provided herein comprise an ion swapping and solvent extraction process followed by a process which functions to recover a fraction rich in gamma-oryzanol to enable the subsequent production of a high purity ferulic acid. In alternative embodiments, methods as provided herein comprise a saponification and solvent extraction process followed by a process which functions to recover a fraction rich in an oryzanol such as γ-oryzanol to enable the subsequent production of a high purity ferulic acid.

BACKGROUND

In the manufacture of rice bran oil, some by-products and waste materials are generated, for example, materials comprising an alkaline oil cake rich in oil components, which is called soapstock. This waste material is known to contain useful components. However, it was customary for this waste materials and other rice bran oil refining by-products to be disposed of as useless industrial waste materials or low value animal feed ingredient because a simple, cost effective technique for effectively utilizing this waste material was unknown in this technical field.

Known methods lead to a considerable consumption of water, low γ-oryzanol yields, significant by-product generation, the use of harmful chemicals and solvents, additional waste generation and uneconomical γ-oryzanol or ferulic acid recovery. Environmental impacts are not optimized and thus contribute to the depletion of groundwater and to the increase of organic loads discharged into the environment. There is a need for a simple, high efficiency process to recover γ-oryzanol and ferulic acid that minimizes or eliminates waste generation, minimizes overall recovery costs and maximizes sellable products.

SUMMARY

In alternative embodiments, provided are methods or processes of manufacturing ferulic acid, and optionally isolating or substantially isolating the ferulic acid, comprising the steps of:
(a) preparing or having provided a raw or starting material comprising an oryzanol, or gamma-oryzanol, (or γ-oryzanol), or a mixture of ferulic acid esters of phytosterols and triterpenoids, optionally comprising cycloartenyl ferulate, 24-methylenecycloartanyl ferulate, and/or campesteryl ferulate,
wherein optionally the raw or starting material comprises or is derived from a plant or microbial (optionally bacterial, algal or fungal) material or byproduct, and optionally the raw or starting material comprises or is derived from a rice bran oil, a rice bran soap stock, a waste material thereof, a plant by-product, or a mixture of said rice bran oil, rice bran soap stock, waste material and by-product generated from the manufacture of rice bran oil,
wherein optionally methods of preparing the raw starting material comprise drying, addition of water, addition of solvent(s) or a combination thereof; and
subjecting the raw or the starting material to a hydrolysis process in the presence of an alkali (or base),
wherein the hydrolysis process comprises the steps of:
(i) mixing the raw or starting material with a first alkali (or base) and agitating or stirring the resultant mixture, optionally while heating (and optionally the raw or starting material and alkali (or base) mixture is heated to between about 20° C. to 200° C., or between about 60° C. to 150° C., or between about 80° C. to 100° C., optionally heated for between about 1 to 240 minutes (min), or between about 30 to 60 min),
wherein optionally sufficient alkali (or base) is added to reach a pH of about 10, or between about pH 8 and 11,
to produce a first saponified mixture and/or one or more derivatives of the first saponified mixture, and
(ii) extracting or substantially extracting the first saponified mixture and/or one or more derivatives of the first saponified mixture with a first solvent so as to remove or substantially remove the materials soluble in said first solvent, thereby creating or generating a first solvent phase,
wherein optionally derivatives comprise fatty acid soaps with a water content of between about 0.01% to 99%,
and optionally a first saponified mixture derivative is formed by combining the first saponified mixture with one or more ion swapping agents to afford or to generate a first precipitate mixture comprising fatty acid soaps with counterions that are monovalent, divalent, or trivalent in nature, or any combination thereof,
and optionally the first solvent comprises water, supercritical $CO_2$, dichloromethane, chloroform, hexane, heptane, methanol, ethanol, isopropanol, butanol, ethyl acetate or a combination thereof, and
(iii) mixing the first saponified mixture with an ion swapping agent and agitating or stirring the resultant mixture, optionally while heating (and optionally the heating or the first saponified mixture is between about 20° C. to 200° C., or between about 60° C. to 150° C., or between about 80° C. to 120° C., optionally heated for between about 1 to 240 minutes (min), or between about 30 to 60 min or 90 to 120 min), therefore to afford or to generate a first precipitate mixture,
wherein optionally the ion swapping agent comprises iron chloride, iron hydroxide, iron sulfate, calcium chloride, calcium hydroxide, calcium sulfate, magnesium chloride, magnesium hydroxide, magnesium sulfate, aluminum chloride, aluminum hydroxide, aluminum sulfate or an equivalent or a combination thereof;

(iv) extracting or substantially extracting the first precipitate mixture and/or first precipitate with a second solvent so as to remove or substantially remove the materials soluble in said second solvent, therefore creating or generating a first solvent phase,
wherein optionally the water from the first precipitate is removed or substantially removed prior to extracting with the second solvent,
and optionally the second solvent comprises hexane, heptane, methanol, ethanol, propanol, isopropanol, a butanol (optionally n-butanol or isobutanol) or a combination thereof, (v) separating the first solvent phase from the first precipitate mixture and/or first precipitate,
wherein optionally the first solvent phase is subjected to one or more additional steps to further purify or substantially purify the oryzanol (or γ-oryzanol), or a mixture of ferulic acid esters of phytosterols and triterpenoids optionally comprising cycloartenyl ferulate, 24-methylenecycloartanyl ferulate, and/or campesteryl ferulate, contained within, therefore creating or generating a first purified oryzanol, (or γ-oryzanol), or mixture of ferulic acid esters of phytosterols and triterpenoids optionally comprising cycloartenyl ferulate, 24-methylenecycloartanyl ferulate, and/or campesteryl ferulate, (vi) mixing a second alkali (or base) with the first solvent phase and agitating or stirring the resultant mixture, optionally while heating (and optionally heating is between about 20° C. to 200° C., or between about 60° C. to 150° C., or between about 80° C. to 100° C., optionally heated for between about 1 to 240 minutes (min), or between about 30 to 60 min or between 60 to 90 min), to generate a second saponified mixture comprising a ferulate salt,
wherein optionally the ferulate salt exists in the liquid phase, solid phase, or both, and (vii) removing the ferulate salt from the second saponified mixture,
wherein optionally if the ferulate salt exists as a solid phase it comprises a solvent that can optionally be recovered,
and optionally the ferulate salt is removed or substantially removed from the second saponified mixture by a process comprising evaporation or filtration or a combination thereof or an equivalent thereof, and (viii) dissolving the ferulate salt in water or an aqueous solution to generate or afford or to generate a first ferulate salt mixture,
wherein optionally, the first ferulate salt mixture comprises impurities that are not water-soluble and can be removed or substantially removed so as to afford or generate a first ferulate salt solution and a first ferulate salt impurity,
and optionally substantially or all impurities that are not water-soluble are removed or substantially removed from the first ferulate salt mixture,
and optionally the first ferulate salt impurity comprises unsaponifiables that can be upgraded or purified,
and
and optionally the unsaponifiable in the first ferulate salt impurity are purified or substantially purified by chromatography, crystallization, liquid-liquid extraction, precipitation or a combination thereof or an equivalent thereof, and (ix) acidifying the ferulate salt mixture (optionally acidifying to between about pH 0 to pH 4, or between about pH 1 and pH 3 or between about pH 2 and pH 2.5) and/or first ferulate salt solution so as to precipitate ferulic acid, and optionally the acidifying comprises use of an organic acid (and optionally the organic acid comprises formic, acetic, oxalic, citric, lactic, uric, malic or tartaric acid) or an inorganic acid (and optionally the inorganic acid comprises sulfuric, hydrochloric, phosphoric or nitric acid),
thereby producing a precipitated (or isolated by precipitation) ferulic acid; and
optionally (x) isolating or substantially isolating the precipitated ferulic acid.

In alternative embodiments, provided are methods or processes of manufacturing ferulic acid, and optionally isolating or substantially isolating the ferulic acid, comprising the steps of:

a) preparing or having provided a raw or starting material comprising an oryzanol, or gamma-oryzanol, (or γ-oryzanol), or a mixture of ferulic acid esters of phytosterols and triterpenoids, optionally comprising cycloartenyl ferulate, 24-methylenecycloartanyl ferulate, and/or campesteryl ferulate,
wherein optionally the raw or starting material comprises or is derived from a plant or microbial (optionally bacterial, algal or fungal) material or byproduct, and optionally the raw or starting material comprises or is derived from a rice bran oil, a rice bran soap stock, a waste material thereof, a plant by-product, or a mixture of said rice bran oil, rice bran soap stock, waste material and by-product generated from the manufacture of rice bran oil,
wherein optionally methods of preparing the raw starting material comprise drying, addition of water, addition of solvent(s) or a combination thereof; and b) subjecting the raw or the starting material to a hydrolysis process in the presence of an alkali (or base), wherein the hydrolysis process comprises the steps of:
(i) mixing the raw or starting material with a first alkali (or base) and agitating or stirring the resultant mixture, optionally while heating (and optionally the heating is between about 20° C. to 200° C., or between about 60° C. to 150° C., or between about 80° C. to 100° C., optionally heated for between about 1 to 240 minutes (min), or between about 30 to 60 min), to produce a first saponified mixture and/or one or more derivatives of the first saponified mixture, and (ii) mixing the first saponified mixture with an ion swapping agent and agitating or stirring the resultant mixture, optionally while heating (and optionally the heating is between about 20° C. to 200° C., or between about 60° C. to 150° C., or between about 80° C. to 100° C., optionally heated for between about 1 to 240 minutes (min), or between about 30 to 60 min) to generate a first solvent phase and a first precipitate mixture, wherein optionally the ion swapping agent comprises iron chloride, iron hydroxide, iron sulfate, calcium chloride, calcium hydroxide, calcium sulfate, magnesium chloride, magnesium hydroxide, magnesium sulfate, aluminum chloride, aluminum hydroxide, aluminum sulfate or an equivalent or a combination thereof;

(iii) separating the first solvent phase from the first precipitate mixture and/or first precipitate, wherein optionally the first solvent phase is subjected to one or more additional steps to further purify or substantially purify the oryzanol (or γ-oryzanol), or a mixture of ferulic acid esters of phytosterols and triterpenoids optionally comprising cycloartenyl ferulate, 24-methylenecycloartanyl ferulate, and/or campesteryl ferulate, contained within, therefore creating or generating a first purified oryzanol, (or γ-oryzanol), or mixture of ferulic acid esters of phytosterols and triterpenoids optionally comprising cycloartenyl ferulate, 24-methylenecycloartanyl ferulate, and/or campesteryl ferulate, (iv) mixing a second alkali (or base) with the first solvent phase (and optionally the amount of alkali (or base) that is added is between about 100% to 300%, or up to about 1,000%, the mass of the oryzanol or a mixture of ferulic acid esters of phytosterols and triterpenoids) and agitating or stirring the resultant mixture, optionally while heating (and optionally the heating is between about 20° C. to 200° C., or between about 50° C. to 150° C., or between about 60° C. to 90° C., or between about 80° C. to 100° C., optionally heated for between about 1 to 240 minutes (min), or between about 30 to 90 min, or about 60 min), to generate a second saponified mixture comprising a ferulate salt, wherein optionally the ferulate salt exists in the liquid phase, solid phase, or both, and (v) removing the ferulate salt from the second saponified mixture, wherein optionally if the ferulate salt exists as a solid phase it comprises a solvent that can optionally be recovered, and optionally the ferulate salt is removed or substantially removed from the second saponified mixture by a process comprising evaporation or filtration or a combination thereof or an equivalent thereof, and (vi) dissolving the ferulate salt in water or an aqueous solution to generate or afford or to generate a first ferulate salt mixture, wherein optionally, the first ferulate salt mixture comprises impurities that are not water-soluble and can be removed or substantially removed so as to afford or generate a first ferulate salt solution and a first ferulate salt impurity, and optionally substantially or all impurities that are not water-soluble are removed or substantially removed from the first ferulate salt mixture, and optionally the first ferulate salt impurity comprises unsaponifiables that can be upgraded or purified, and and optionally the unsaponifiable in the first ferulate salt impurity are purified or substantially purified by chromatography, crystallization, liquid-liquid extraction, precipitation or a combination thereof or an equivalent thereof, and (vii) acidifying the ferulate salt mixture and/or first ferulate salt solution (optionally acidifying to between about pH 0 to pH 4, or between about pH 1 and pH 3 or between about pH 2 and pH 2.5) so as to precipitate ferulic acid, and optionally the acidifying comprises use of an organic acid (and optionally the organic acid comprises formic, acetic, oxalic, citric, lactic, uric, malic or tartaric acid) or an inorganic acid (and optionally the inorganic acid comprises sulfuric, hydrochloric, phosphoric or nitric acid), thereby producing a precipitated (or isolated by precipitation) ferulic acid; and optionally (viii) isolating or substantially isolating the precipitated ferulic acid.

In alternative embodiments of methods as provided herein:

the raw or starting material comprises a rice bran soap stock generated from a chemical refining of a crude rice bran oil from a rice bran;

the raw or starting material comprises an alkaline oil cake generated from a chemical refining of a crude rice bran oil from a rice bran;

the raw or starting material comprises a rice bran and/or a derivative of the rice bran;

the raw or starting material is a physically refined rice bran oil generated from a physical refining of a crude rice bran oil from a rice bran;

the alkali (or base) used in a hydrolysis step comprises: an oxide, hydroxide, carbonate, bicarbonate or a mixture or an equivalent thereof;

the ion swapping agent comprises reagents comprising calcium, magnesium, aluminum, iron, or a mixture or an equivalent thereof;

the first precipitate mixture is further separated into a first precipitate and a first brine solution;

the hydrolysis can be conducted in the presence of solvent, and optionally the solvent comprises at least one alcohol or a plurality of alcohols;

the alcohol solvent comprises a butanol, optionally an n-butanol or an isobutanol;

a ferulic acid having a purity of about 50% or greater, or between about 45% and 100%, or between about 40% and 95%, is produced;

the first solvent phase is subjected to one or more operations comprising evaporation, ion exchange, chromatography, crystallization, or an equivalent or any combination thereof;

the ferulic acid comprises or is trans-ferulic acid;

the produced ferulic acid is used to manufacture vanillin (or 4-hydroxy-3-methoxybenzaldehyde), ethylvanillin, acetovanillone and/or conjugates or derivatives of vanillin, and optionally the vanillin, ethylvanillin, acetovanillone and/or conjugates or derivatives of vanillin are produced using a method comprising fermentation by an organism, for example as described by Ciriminna, et al., Chemistry Open. 2019 June; 8(6): 660-667, or optionally a microorganism, a bacteria or a yeast, optionally a recombinantly modified microorganism is engineered to convert ferulic acid to vanillin, ethylvanillin, acetovanillone and/or conjugates or derivatives of vanillin, optionally a microorganism engineered to express a heterologous feruloyl-CoA synthetase and feruloyl-CoA hydratase/aldolase, as described for example by Luziatelli et al., Front. Bioeng. Biotechnol., 18 Oct. 2019.

In alternative embodiments, provided are methods of manufacturing ferulic acid, comprising the steps of:

(a) preparing or having provided a raw or starting material comprising oryzanol, or gamma-oryzanol (or γ-oryzanol), or a mixture of ferulic acid esters of phytosterols and triterpenoids, optionally comprising cycloartenyl ferulate, 24-methylenecycloartanyl ferulate, and/or campesteryl ferulate, wherein optionally the raw or starting material comprises or is derived from a plant or microbial (optionally bacterial, algal or fungal) material or byproduct, and optionally the raw or starting material comprises or is derived from a rice bran oil, a rice bran soap stock, a waste material thereof, a plant by-product, or a mixture of said rice bran oil, rice bran soap stock, waste material and by-product generated from the manufacture of rice bran oil, wherein optionally methods of preparing the raw starting material comprise drying, addition of water, addition of solvent(s) or a combination thereof; and (b) subjecting the raw or starting material to a hydrolysis process in the presence of an alkali (or base) or an enzyme, wherein optionally sufficient alkali (or base) is added to reach a pH of about 10, or between about pH 8 and 11, wherein the hydrolysis process comprises the steps of:

(i) mixing the raw or starting material with a first alkali (or base) or an enzyme and agitating or stirring the resultant mixture, optionally while heating (and optionally the enzyme mixture is heated to between about 20° C. to 200° C., or between about 60° C. to 150° C., or between about 80° C. to 100° C., optionally heated for between about 1 to 240 minutes (min), or between about 30 to 60 min), to produce a first hydrolyzed mixture or first saponified mixture and/or one or more derivatives of the first hydrolyzed mixture or first saponified mixture, and and optionally drying or substantially drying the first hydrolyzed mixture or first saponified mixture (ii) extracting or substantially extracting the first saponified mixture and/or one or more derivatives of the first saponified mixture with a first solvent so as to remove or substantially remove the materials soluble in said first solvent, thereby creating or generating a first solvent phase, wherein optionally derivatives comprise fatty acid soaps with a water content of between about 0.01% to 99%, and optionally repeating step ii) to create multiple first solvent phases.

and optionally the first solvent comprises water, supercritical $CO_2$, dichloromethane, chloroform, hexane, heptane, methanol, ethanol, isopropanol, butanol, ethyl acetate or a combination thereof, and (iii) removing or substantially removing the solvent from first solvent phase to generate a first extract, and (iv) mixing the first extract an enzyme, and, optionally mixing with a solvent to effect hydrolysis of the contained oryzanol into sterols and ferulate/ferulic acid so as to create a first ferulic mixture, wherein, optionally heating the first extract and enzyme mixture (with or without a solvent) to accelerate the oryzanol hydrolysis rate, and optionally, the solvent comprises water, supercritical CO2, dichloromethane, chloroform, hexane, heptane, methanol, ethanol, isopropanol, butanol, ethyl acetate or a combination thereof, and (v) adding a basic solution to the hydrolyzed mixture to extract the ferulate/ferulic acid, therefore to afford or to generate a first ferulate salt mixture, wherein optionally, the base is added neat (or undiluted) or as a solution in water or polar solvent (and optionally the polar solvent comprises methanol, ethanol, propanol, butanol or a combination thereof) with a pH of between about pH 7 to pH 14, and optionally, the first ferulate salt mixture comprises impurities that are not soluble in the basic mixture and can be removed so as to afford or to generate a first ferulate salt solution and a first ferulate salt impurity, and optionally the first ferulate salt impurity comprises unsaponifiables that can be upgraded or purified, (vi) acidifying the basic ferulate salt solution (optionally acidifying to between about pH 0 to pH 4, or between about pH 1 and pH 3 or between about pH 2 and pH 2.5) to precipitate ferulic acid with high purity (or optionally to a purity of about 70%, 75%, 80%, 85% or 90% or more or a purity of between about 65% to 99%) from a now acidified solution, and optionally the acidifying comprises use of an organic acid (and optionally the organic acid comprises formic, acetic, oxalic, citric, lactic, uric, malic or tartaric acid) or an inorganic acid (and optionally the inorganic acid comprises sulfuric, hydrochloric, phosphoric or nitric acid); and (vii) recovering or substantially recovering high purity ferulic acid by filtration, washing to remove or substantially remove residual acidified solution from the ferulic acid, and drying or substantially drying to less than 5% volatile content, therefore generating a high-purity, bio-based ferulic acid for use as-is or for production of a ferulic acid derivative, and optionally the ferulic acid derivative comprise a bio-based vanillin, ethylvanillin, acetovanillone and/or conjugates or derivatives of vanillin, optionally that qualify as naturally a produced vanillin, optionally according to EC Regulation 1334/2008 of the European Parliament and of the Council, and optionally the vanillin, ethylvanillin, acetovanillone and/or conjugates or derivatives of vanillin are produced using a method comprising fermentation by an organism, for example as described by Ciriminna, et al., Chemistry Open. 2019 June; 8(6): 660-667, or optionally a microorganism, a bacteria or a yeast, optionally a recombinantly modified microorganism is engineered to convert ferulic acid to vanillin, ethylvanillin, acetovanillone and/or conjugates or derivatives of vanillin, optionally a microorganism engineered to express a heterologous feruloyl-CoA synthetase and feruloyl-CoA hydratase/aldolase, as described for example by Luziatelli et al., Front. Bioeng. Biotechnol., 18 Oct. 2019.

In alternative embodiments of methods as provided herein:

the raw or starting material comprises a rice bran soap stock generated from a chemical refining of a crude rice bran oil from a rice bran;

the raw or starting material is an alkaline oil cake generated from a chemical refining of a crude rice bran oil from a rice bran;

the raw or starting material comprises a rice bran and/or a derivative of the rice bran;

the raw or starting material is a physically refined rice bran oil generated from a physical refining of a crude rice bran oil from a rice bran;

the alkali (or base) used in a hydrolysis step comprises: an oxide, hydroxide, carbonate, bicarbonate or a mixture or an equivalent thereof;

the hydrolysis can be conducted in the presence of water and enzyme, and a ferulic acid having a purity of at least about 50% or greater, or between about 45% and 90%, or between about 40% and 99%, is produced;

the first solvent phase is subjected to one or more operations comprising evaporation, ion exchange, chromatography, crystallization, or an equivalent or any combination thereof;

the ferulic acid comprises or is trans-ferulic acid;

the produced ferulic acid is used to make or manufacture vanillin (or 4-hydroxy-3-methoxybenzaldehyde), ethylvanillin, acetovanillone and/or conjugates or derivatives of vanillin, or optionally the method further comprises using the produced ferulic acid to make or produce vanillin (or 4-hydroxy-3-methoxybenzaldehyde), ethylvanillin, acetovanillone and/or conjugates or derivatives of vanillin, and optionally the vanillin, ethylvanillin, acetovanillone and/or conjugates or derivatives of vanillin are produced using a method comprising fermentation by an organism, for example as described by Ciriminna, et al., Chemistry Open. 2019 June; 8(6): 660-667, or optionally a microorganism, a bacteria or a yeast, optionally a recombinantly modified microorganism is engineered to convert ferulic acid to vanillin, ethylvanillin, acetovanillone and/or conjugates or derivatives of vanillin, optionally a microorganism engineered to express a heterologous feruloyl-CoA synthetase and feruloyl-CoA hydratase/aldolase, as described for example by Luziatelli et al., Front. Bioeng. Biotechnol., 18 Oct. 2019.

In alternative embodiments, provided are methods of preparing or manufacturing ferulic acid, comprising the steps of:

(a) preparing or having provided a raw or starting material comprising oryzanol, or gamma-oryzanol, (or γ-oryzanol), or a mixture of ferulic acid esters of phytosterols and triterpenoids, optionally comprising cycloartenyl ferulate, 24-methylenecycloartanyl ferulate, and/or campesteryl ferulate, wherein optionally the raw or starting material comprises or is derived from a plant or microbial (optionally bacterial, algal or fungal) material or byproduct, and optionally the raw or starting material comprises or is derived from a rice bran oil, a rice bran soap stock, a waste material thereof, a plant by-product, or a mixture of said rice bran oil, rice bran soap stock, waste material and by-product generated from the manufacture of rice bran oil; and optionally, methods of preparing the starting material comprise drying, addition of water, addition of solvent(s); and (b) subjecting the raw or starting material to a hydrolysis process in the presence of an alkali (or base), or an alkali hydrolysis, wherein optionally sufficient alkali is added to reach a pH of about 10, or between about pH 8 and 11, wherein the hydrolysis process comprises the steps of:

(i) mixing the raw or starting material with a first alkali (or base) and agitating or stirring the resultant mixture, optionally while heating (and optionally the raw or starting material and alkali mixture is heated to between about 20° C. to 200° C., or between about 60° C. to 150° C., or between about 80° C. to 100° C., optionally heated for between about 1 to 240 minutes (min), or between about 30 to 60 min), to produce a first saponified mixture and/or one or more derivatives of the first saponified mixture, and and optionally drying the first saponified mixture (ii) extracting the first saponified mixture and/or one or more derivatives of the first saponified mixture with a first solvent so as to remove or substantially remove the materials soluble in said first solvent, thereby creating or generating a first solvent phase, wherein optionally derivatives comprise fatty acid soaps with a water content of between about 0.01% to 99%, and optionally repeating step ii to create multiple first solvent phases.

and optionally the first solvent comprises water, supercritical CO2, dichloromethane, chloroform, hexane, heptane, methanol, ethanol, isopropanol, butanol, ethyl acetate or a combination thereof, and (iii) removing the solvent from first solvent phase to generate a first extract, and (iv) mixing the first extract with water and an enzyme and, optionally heating and agitating or stirring the first extract and enzyme mixture to effect hydrolysis of the contained oryzanol (or γ-oryzanol), or a mixture of ferulic acid esters of phytosterols and triterpenoids optionally comprising cycloartenyl ferulate, 24-methylenecycloartanyl ferulate, and/or campesteryl ferulate, and optionally adding an cation to the mixture wherein anions comprise potassium, phosphorous, sodium or mixtures thereof, and (v) precipitating, crystalizing or filtering the resulting ferulate salt from the mixture, and (vi) dissolving or substantially dissolving the ferulate salt in water or an aqueous solution to generate a first ferulate salt mixture, wherein optionally, the first ferulate salt mixture comprises impurities that are not water-soluble and can be removed or substantially removed so generate a first ferulate salt solution and a first ferulate salt impurity, and optionally the first ferulate salt impurity comprises unsaponifiables that can be upgraded or purified, and optionally the unsaponifiable in the first ferulate salt impurity are purified by chromatography, crystallization, liquid-liquid extraction, precipitation or a combination thereof or an equivalent thereof, and (vii) acidifying the ferulate salt mixture and/or first ferulate salt solution (optionally acidifying to between about pH 0 to pH 4, or between about pH 1 and pH 3 or between about pH 2 and pH 2.5) so as to precipitate ferulic acid, and optionally the acidifying comprises use of an organic acid (and optionally the organic acid comprises formic, acetic, oxalic, citric, lactic, uric, malic or tartaric acid) or an inorganic acid (and optionally the inorganic acid comprises sulfuric, hydrochloric, phosphoric or nitric acid), thereby producing a purified, precipitated ferulic acid; and optionally (viii) isolating or substantially isolating or purifying the precipitated ferulic acid.

In alternative embodiments of methods as provided herein:

the raw or starting material comprises a rice bran soap stock generated from a chemical refining of a crude rice bran oil from a rice bran;

the raw or starting material is an alkaline oil cake generated from a chemical refining of a crude rice bran oil from a rice bran;

the raw or starting material comprises a rice bran and/or a derivative of the rice bran;

the raw or starting material is a physically refined rice bran oil generated from a physical refining of a crude rice bran oil from a rice bran;

the alkali (or base) used in a hydrolysis step comprises: an oxide, hydroxide, carbonate, bicarbonate or a mixture or an equivalent thereof;

the hydrolysis can be conducted in the presence of water and enzyme, and a ferulic acid having a purity of about 50% or greater, or between about 45% and 100%, or between about 40% and 99% or 100%, is produced;

the first solvent phase is subjected to one or more operations comprising evaporation, ion exchange, chromatography, crystallization, or an equivalent or any combination thereof;

the ferulic acid comprises or is trans-ferulic acid;

the produced ferulic acid is used to manufacture vanillin (or 4-hydroxy-3-methoxybenzaldehyde), ethylvanillin, acetovanillone and/or conjugates or derivatives of vanillin, and optionally the vanillin, ethylvanillin, acetovanillone and/or conjugates or derivatives of vanillin are produced using a method comprising fermentation by an organism, for example as described by Ciriminna, et al., Chemistry Open. 2019 June; 8(6): 660-667, or optionally a microorganism, a bacteria or a yeast, optionally a recombinantly modified microorganism is engineered to convert ferulic acid to vanillin, ethylvanillin, acetovanillone and/or conjugates or derivatives of vanillin, optionally a microorganism engineered to express a heterologous feruloyl-CoA synthetase and feruloyl-CoA hydratase/aldolase, as described for example by Luziatelli et al., Front. Bioeng. Biotechnol., 18 Oct. 2019.

In alternative embodiments, provided are methods or processes of manufacturing ferulic acid, comprising the steps of:

(a) preparing a raw or starting material comprising oryzanol, or γ-oryzanol, or a mixture of ferulic acid esters of phytosterols and triterpenoids, optionally comprising cycloartenyl ferulate, 24-methylenecycloartanyl ferulate, and/or campesteryl ferulate, wherein optionally the raw or starting material comprises or is derived from a plant material or byproduct, and optionally the raw material comprises or is derived from a rice bran oil, a rice bran soap stock, a waste material thereof, a plant by-product, or a mixture of said rice bran oil, rice bran soap stock, waste material and by-product generated from the manufacture of rice bran oil; and (b) subjecting the raw material to alkali (or base) hydrolysis thereby converting substantially all of the remaining glycerides to alkali soaps, and optionally drying the resulting material from step a, and (c) solvent extracting the material from step b and or c, and (d) removing or substantially removing the solvent from step c to generate a first solvent extract containing oryzanol, and (e) subjecting the γ-oryzanol-containing raw material to a hydrolysis process in the presence of an enzyme or mixture of enzymes, and water or water and a polar solvent (and optionally the polar solvent comprises methanol, ethanol, propanol, butanol or a combination thereof), wherein the hydrolysis process comprises the steps of:

(i) mixing the raw material with a first enzyme or mixture of enzymes and agitating or stirring the resultant mixture, optionally while heating (optionally heating for between about 1 to 240 minutes (min), or between about 30 to 60 min), to produce a first hydrolyzed mixture, and (ii) extracting or substantially extracting ferulic acid from the first hydrolyzed mixture and/or one or more derivatives of the first hydrolyzed mixture with a first cation to create a ferulate salt so as to remove or substantially remove the materials that are insoluble in said first hydrolyzed mixture, thereby creating or generating a first precipitate phase, wherein optionally steps i) and ii) are repeated, and the precipitate ferulate salt is removed or substantially removed from the precipitate phase, optionally by a process comprising solvent extraction, crystallization or filtration or a combination thereof, and optionally the solvent comprises water, supercritical $CO_2$, dichloromethane, chloroform, hexane, heptane, methanol, ethanol, isopropanol, butanol, ethyl acetate or a combination thereof, and wherein optionally the water from the first precipitate is removed or substantially removed prior to extracting with the second solvent, and optionally the second solvent comprises hexane, heptane, methanol, ethanol, propanol, isopropanol, a butanol (optionally n-butanol or isobutanol) or a combination thereof, (iii) separating or substantially separating the first solvent phase from the first precipitate mixture and/or first precipitate, wherein optionally the first solvent phase is subjected to one or more additional steps to further purify the oryzanol contained within, therefore creating or generating a first purified oryzanol, wherein optionally if the ferulate salt exists as a solid phase it comprises a solvent that can optionally be recovered or substantially recovered, (iv) dissolving the ferulate salt in water or an aqueous solution to generate a first ferulate salt mixture, wherein optionally, the first ferulate salt mixture comprises impurities that are not water-soluble and can be removed or substantially removed so as to afford or to generate a first ferulate salt solution and a first ferulate salt impurity, and optionally the first ferulate salt impurity comprises unsaponifiables that can be upgraded or purified, and optionally the unsaponifiable in the first ferulate salt impurity are purified or substantially purified, optionally purified or substantially purified by a process comprising chromatography, crystallization, liquid-liquid extraction, precipitation or a combination thereof or an equivalent thereof, (v) acidifying the ferulate salt mixture and/or first ferulate salt solution (optionally acidifying to between about pH 0 to pH 4, or between about pH 1 and pH 3 or between about pH 2 and pH 2.5) so as to precipitate or substantially precipitate ferulic acid, and optionally the acidifying comprises use of an organic acid (and optionally the organic acid comprises formic, acetic, oxalic, citric, lactic, uric, malic or tartaric acid) or an inorganic acid (and optionally the inorganic acid comprises sulfuric, hydrochloric, phosphoric or nitric acid); and (vi) isolating (or purifying) or substantially isolating (or purifying) the precipitated ferulic acid.

In alternative embodiments, provided are methods of producing bio-based ferulic acid for use as-is or for production of ferulic acid derivatives, and optionally the ferulic acid derivative comprises a vanillin, ethylvanillin, acetovanillone and/or conjugates or derivatives of vanillin, comprising the steps of:

(a) preparing a raw or starting material comprising an oryzanol, optionally γ-oryzanol, or a mixture of ferulic acid esters of phytosterols and triterpenoids, optionally comprising cycloartenyl ferulate, 24-methylenecycloartanyl ferulate, and/or campesteryl ferulate, wherein optionally the raw or starting material comprises or is derived from a plant or microbial (optionally bacterial, algal or fungal) material or byproduct, and optionally the raw or starting material comprises or is derived from a rice bran oil, a rice bran soap stock, a waste material thereof, a plant by-product, or a mixture of said rice bran oil, rice bran soap stock, waste material and by-product generated from the manufacture of rice bran oil; and optionally, methods of preparing the raw or starting material comprise drying, addition of water, addition of solvent(s); and (b) subjecting the oryzanol (or γ-oryzanol)-containing, or mixture of ferulic acid esters of phytosterols and triterpenoids, optionally comprising cycloartenyl ferulate, 24-methylenecycloartanyl ferulate, and/or campesteryl ferulate-comprising, raw or starting material to a glyceride hydrolysis process in the presence of an enzyme or alkali (or base), wherein the glyceride hydrolysis process comprises the steps of:

(i) mixing the raw or starting material with an enzyme or first alkali (or base) and agitating the resultant mixture, optionally while heating (and optionally the raw or starting material and alkali (or base) and/or enzyme mixture is heated to between about 20° C. to 200° C., or between about 60° C. to 150° C., or between about 80° C. to 100° C., optionally heating for between about 1 to 240 minutes (min), or between about 30 to 60 min), to produce a first hydrolyzed mixture or first saponified mixture and/or one or more derivatives of the first hydrolysis mixture or first saponified mixture, and optionally, adjusting the pH to between 8 and 11 and drying the first hydrolyzed mixture or first saponified mixture (ii) extracting or substantially extracting the first saponified mixture and/or one or more derivatives of the first saponified mixture with a first solvent so as to remove or substantially remove the materials soluble in said first solvent, thereby creating or generating a first solvent phase, wherein optionally derivatives comprise fatty acid soaps with a water content of between about 0.01% to 99%, and optionally repeating step iii to create multiple solvent phases.

and optionally the first solvent comprises water, supercritical $CO_2$, dichloromethane, chloroform, hexane, heptane, methanol, ethanol, isopropanol, butanol, ethyl acetate or a combination thereof, and (iii) removing or substantially removing the solvent from the first solvent phase to generate a first extract, and (iv) mixing the first extract with an enzyme, and, optionally, a solvent to effect hydrolysis of (all or substantially all of) the contained oryzanol into sterols and ferulate/ferulic acid so as to create a first ferulic mixture, wherein optionally, heating the first extract and enzyme mixture (with or without a solvent) (and optionally the extract and enzyme mixture is heated to between about 20° C. to 200° C., or between about 60° C. to 150° C., or between about 80° C. to 100° C., optionally heating for between about 1 to 240 minutes (min), or between about 30 to 60 min) to accelerate the oryzanol hydrolysis rate, and optionally, the solvent comprises water, supercritical $CO_2$, dichloromethane, chloroform, hexane, heptane, methanol, ethanol, isopropanol, butanol, ethyl acetate or a combination thereof, and (v) adding a basic solution to the hydrolyzed mixture to extract the ferulate/ferulic acid, thereby generating a first ferulate salt mixture, wherein optionally, the base is added neat or as a solution in water or an aqueous solution or polar solvent (and optionally the polar solvent comprises methanol, ethanol, propanol, butanol or a combination thereof) having a pH of between about pH of 7 to about a pH of 14, and optionally, the first ferulate salt mixture comprises impurities that are not soluble in the basic mixture and can be removed or substantially removed so as to afford or to generate a first ferulate salt solution and a first ferulate salt impurity, and optionally the first ferulate salt impurity comprises unsaponifiables that can be upgraded or purified, and optionally the unsaponifiables in the first ferulate salt impurity are purified by chromatography, crystallization, liquid-liquid extraction, precipitation or a combination thereof or an equivalent thereof, and (vi) acidifying the basic ferulate salt solution (optionally acidifying to between about pH 0 to pH 4, or between about pH 1 and pH 3 or between about pH 2 and pH 2.5) to precipitate ferulic acid with high purity (70%, 75%, 80%, 85% or 90% or greater) from a now acidified solution, and optionally the acidifying comprises use of an organic acid (and optionally the organic acid comprises formic, acetic, oxalic, citric, lactic, uric, malic or tartaric acid) or an inorganic acid (and optionally the inorganic acid comprises sulfuric, hydrochloric, phosphoric or nitric acid); and (vii) recovering or substantially recovering high purity ferulic acid by filtration, washing to remove residual acidified solution from the ferulic acid, and drying or substantially drying optionally to less than about 5% volatile content, therefore affording (or thereby generating) high-purity, bio-based ferulic acid for use as-is or for production of a ferulic acid derivative, wherein optionally the ferulic acid derivative comprises a bio-based vanillin, ethylvanillin, aceto-vanillone and/or conjugates or derivatives of vanillin, that optionally qualify as naturally produced vanillin, optionally according to EC Regulation 1334/2008 of the European Parliament and of the Counci, and optionally the vanillin, ethylvanillin, acetovanillone and/or conjugates or derivatives of vanillin are produced using a method comprising fermentation by an organism, for example as described by Ciriminna, et al., Chemistry Open. 2019 June; 8(6): 660-667, or optionally a microorganism, a bacteria or a yeast, optionally a recombinantly modified microorganism is engineered to convert ferulic acid to vanillin, ethylvanillin, acetovanillone and/or conjugates or derivatives of vanillin, optionally a microorganism engineered to express a heterologous feruloyl-CoA synthetase and feruloyl-CoA hydratase/aldolase, as described for example by Luziatelli et al., Front. Bioeng. Biotechnol., 18 Oct. 20191.

The details of one or more exemplary embodiments of the invention are set forth in the accompanying drawings and the description below. Other features, objects, and advantages of the invention will be apparent from the description and drawings, and from the claims.

All publications, patents, patent applications cited herein are hereby expressly incorporated by reference in their entireties for all purposes.

DESCRIPTION OF DRAWINGS

The drawings set forth herein are illustrative of exemplary embodiments provided herein and are not meant to limit the scope of the invention as encompassed by the claims.

Like reference symbols in the various drawings indicate like elements.

DETAILED DESCRIPTION OF THE INVENTION

Figure 1:
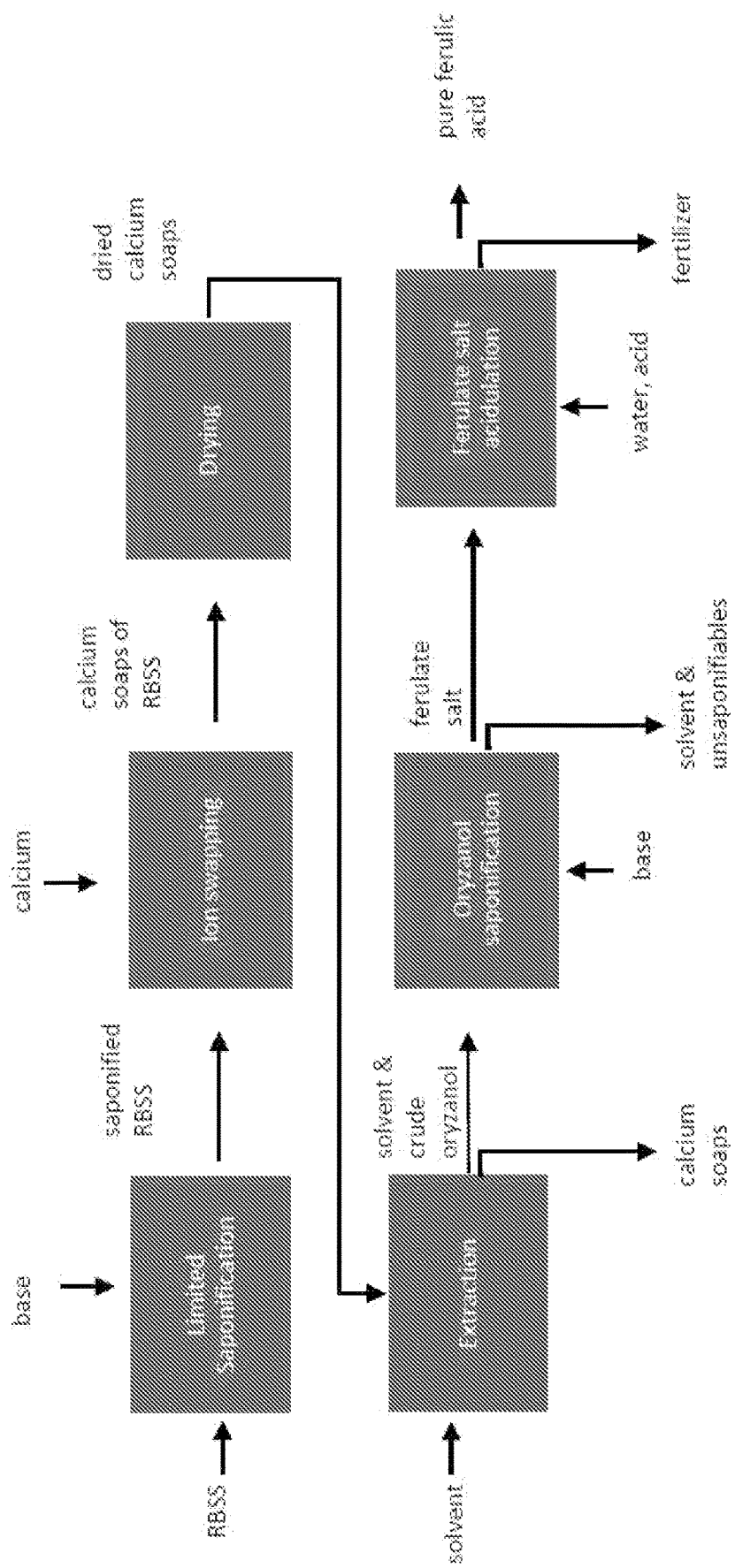
FIG. 1 schematically illustrates exemplary steps included in exemplary methods as provided herein, as described in further detail below.
Figure 2:
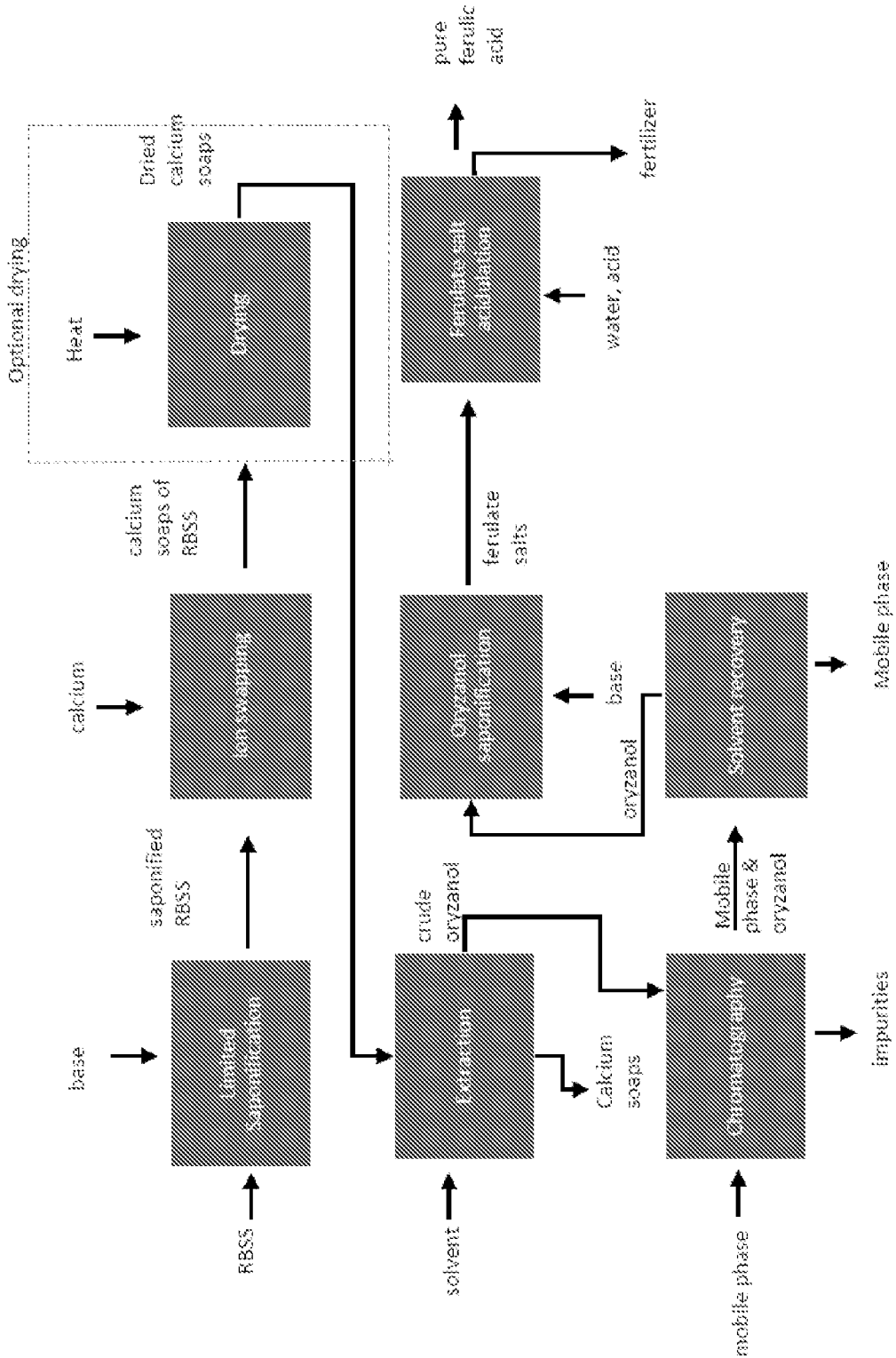
FIG. 2 schematically illustrates exemplary steps included in exemplary methods as provided herein, as described in further detail below.
Figure 3:
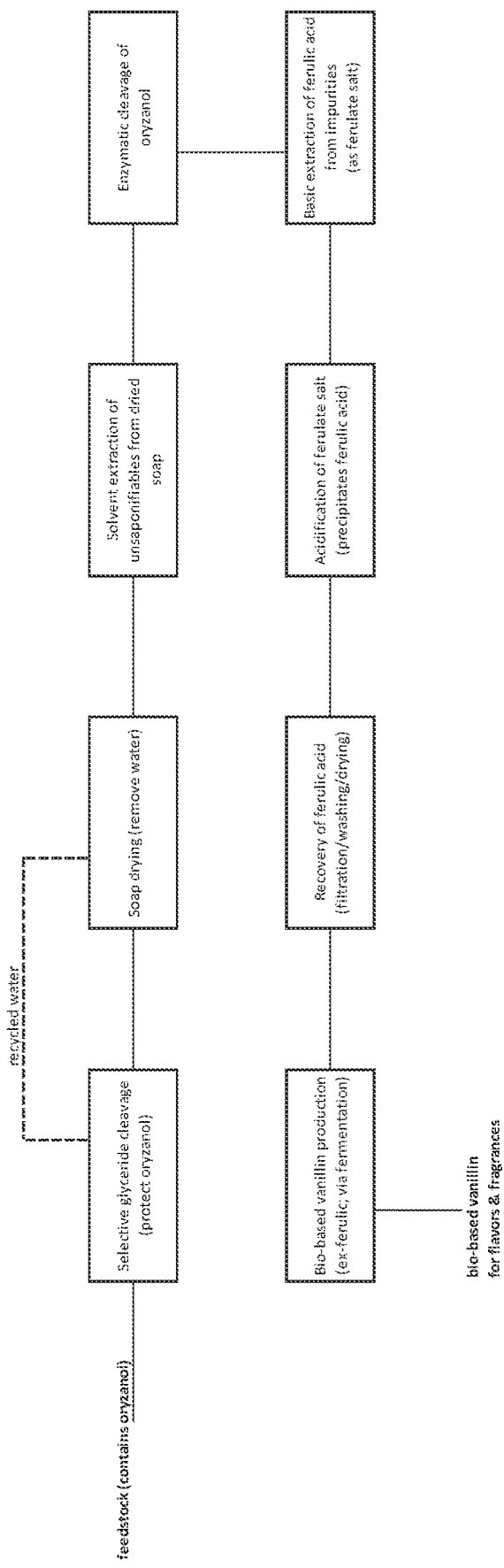
FIG. 3 schematically illustrates exemplary steps included in exemplary methods as provided herein, as described in further detail below.

In alternative embodiments, provided are methods of making or manufacturing, and optionally also isolating or purifying, ferulic acid, or (E)-3-(4-hydroxy-3-methoxy-phenyl)prop-2-enoic acid, which then can be used as a raw or starting material for the manufacture of, for example, medicines, agricultural chemicals, cosmetics, pigments, and food additives such as for example derivatives of ferulic acid such as vanillin.

In alternative embodiments, provided are methods for the treatment of a plant material or plant extract or by-product, for example, a rice bran or rice bran oil, for the purpose of extracting high purity oryzanol such as gamma-oryzanol ($\gamma$-oryzanol) or a ferulic acid ester of a phytosterol from it in order to utilize the natural ferulic acid as part of the oryzanol as a raw or starting material in various types of industries, for example in the chemical, cosmetic, pharmaceutical, biotechnology or food processing industries. In alternative embodiments, provided are methods and processes for the recovery or purification of the natural ferulic acid present in a plant starting material such as rice bran oil and/or rice bran oil soap stock, which then can be used to produce derivatives of ferulic acid, including flavors such as food flavors, for example, vanillin.

In alternative embodiments, provided are methods for manufacturing ferulic acid by isolating or substantially isolating or purifying oryzanol contained in a rice bran oil or a rice bran oil chemical refining soap stock (RBSS) and directly extracting oryzanol from the rice bran oil, RBSS or waste materials or by-products, as noted above.

In alternative embodiments, methods as provided herein address the deficiencies and defects encountered in the practice of known methods; for example, in alternative embodiments, provided are methods comprising a clean extraction of oryzanol followed by the production of ferulic acid with improved purity and increased yield. In alternative embodiments, the ferulic acid thus obtained is advantageously converted to natural vanillin by a biofermentation process.

In alternative embodiments, methods as provided herein can use as a starting material any oryzanol-comprising organic material, including an oryzanol-comprising plant material or plant extract or by-product, such as for example rice bran, rice bran oil or rice bran oil chemical refining soap stock (RBSS). RBSS from Rice Bran Oil (RBO) used in methods as provided herein can contain about 65 to 70 wt % water, about 20 to 22 wt % soap, about 2 to 2.5 wt % glycerides (mainly Triglycerides or TG), and about 7 to 7.5 wt % unsaponified matter. The unsaponified fraction can comprise about 42% sterols, about 24% higher fatty alcohols, about 20% oryzanol (as ferulic acid esters), about 10% hydrocarbons, and about 2% unidentified compounds. Oryzanol can comprise about 15% (or about 2% of 7.5 wt %) of the unsaponified matter.

In alternative embodiments, rice bran oil (RBO) used in methods as provided herein can be obtained by either physical or chemical refining. In physical refining first metal complexes can be removed or substantially removed by hydration. The crude rice bran oil is then subjected to the application of physical refining steam distillation technique: that is, under high vacuum conditions, using the partial pressure of water vapor to reduce the partial pressure of free fatty acid in the oil, i.e. reduced boiling temperature of free fatty acids, so that the free fatty acids can be removed or substantially removed at a lower temperature from the oil which remains in its liquid state. The physically refined oil can then be further processed by methods comprising bleaching clay, activated carbon for color and/or odor reduction. The high molecular weight oryzanol remains substantially in the physically refined rice bran oil.

In alternative embodiments, as with general chemical refining of an alkaline substance, sodium hydroxide (NaOH) and water is used to neutralize the acidic free fatty acids present in the crude rice bran oil, and optionally the sodium soaps of free fatty acids are then removed or substantially removed by decantation or centrifuge. In contrast, in methods as provided herein, physiologically active substances comprising oryzanol will report to the rice bran oil soapstock (i.e., oryzanol is removed or substantially removed from rice bran oil during neutralization and concentrated in the soapstock, this still requiring use of alkaline substance such as NaOH). The chemically refined rice bran oil is then, optionally, contacted with bleaching clay to remove or substantially remove color bodies and high molecular weight waxes. The chemically refined and/or bleached rice bran oil can then be steam distillation technique: that is, under high vacuum conditions, using the partial pressure of water vapor to reduce the partial pressure of free fatty acid in the oil, i.e. reduced boiling temperature of free fatty acids, so that the free fatty acids can be removed or substantially removed at a lower temperature from the oil which remains in its liquid state.

A known process for purifying ferulic acid is described in U.S. Pat. No. 9,745,541 B1 "Methods for making free fatty acids from soaps using thermal hydrolysis followed by acidification" or Soap Carbonate Technology (SCT). The biggest unknown of this approach was the survivability of ORZ in the 260° C. for 30 minutes thermal hydrolysis environment. We conducted experiments examining the behavior of RBSS when processed via the SCT pathway. It was determined that most of oryzanol did not survive the 260° C. temperature for 30 minutes of thermal hydrolysis environment. The starting feedstock contained (6.4 wt % or 8.7 g ORZ) and after the reaction was complete the oryzanol was quantified to reveal that 0.73 g of crude oryzanol had survived which represents a great than 90% loss of oryzanol. We determined that RBSS does not behave well in the SCT process. Since ferulic acid via oryzanol is the main product of interest and not fatty acids, the SCT process was abandoned in favor of processes as provided herein, which are capable of preserving the oryzanol for ferulic acid production.

In alternative embodiments, provided are methods wherein a feedstock containing oryzanol, such as rice bran soapstock is first contacted with an alkali (or base), optionally sodium hydroxide or sodium carbonate, to fully convert the glyceride and phospholipid fatty acids present to their salt or soap form, but maintaining the oryzanol in its unconverted or ester form, which requires a pH greater than 10.5 to saponify, and optionally using a pH of 12 or greater. This selective saponification can be achieved by the controlled addition of a base such as sodium hydroxide to a pH of about 9.5 to 10.5.

In alternative embodiments, provided are methods wherein a feedstock containing oryzanol, such as rice bran soapstock, is first contacted with an enzyme, such as a lipase, to fully convert the glyceride and phospholipid fatty acids present to their fatty acid form, but maintaining the oryzanol in its unconverted or ester form. Alkali is then added to convert the fatty acids to soluble fatty soaps, which can be achieved by the controlled addition of a base such as sodium hydroxide to a pH of about 9.5 to 10.5. If preferred, insoluble fatty soaps can also be formed by the controlled addition of a base such as calcium hydroxide to the fatty acids.

In alternative embodiments, sodium hydroxide or potassium hydroxide can be used as an alkali or base in the step of hydrolyzing the glycerides and phospholipids. In alternative embodiments, the resulting mixture of alkali soaps, including for example sodium soaps of the fatty acids existing in the RBSS, is a homogenous mixture with the water present. Once this mixture has been prepared, the ion swapping agent, which optionally can comprise calcium chloride, is added, and this can convert the sodium soaps present to insoluble calcium salts or calcium soaps of fatty acids. This resulting calcium soap or calcium salt of fatty acids mixture, rich in oryzanol, is insoluble in water and precipitates from the water present. The water is optionally removed or substantially removed by filtration or optionally the calcium soap fraction is dried to substantially remove or substantially remove the water.

In alternative embodiments, the calcium soap precipitate containing oryzanol is then mixed with an extraction solvent, optionally an alcohol such as a butanol (for example, n-butanol), which extracts the oryzanol and unsaponifiable components to the alcohol or butanol phase. The solvent phase rich in oryzanol is then either left as-is or is concentrated.

In alternative embodiments, the alcohol phase rich in oryzanol is subjected to a chromatographic step. Optionally, the oryzanol rich fraction is then subjected to chromatography to produce one or more oryzanol fractions.

In alternative embodiments, the solvent phase, depending on the purity of the oryzanol and the presence of impurities comprising glycerides, phospholipids and other materials is left in the solvent extract solution, and can be directly saponified with a base, optionally a strong base such as potassium hydroxide to achieve a pH greater than 10.5, or optionally a pH of greater than 12, to form the ferulate salt. In alternative embodiments, the ferulate salt can then be recovered as a precipitate solid and the impurities comprising sterols and other unsaponifiable matter remain in the extraction solvent.

In alternative embodiments, if the chromatography process is performed, the one or more fractions rich in oryzanol are collected and then either left as-is or concentrated to recycle the mobile phase. In alternative embodiments, the one or more mobile phase fractions rich in oryzanol are then mixed with an alkali or base, optionally potassium hydroxide, achieving a pH greater than about 10.5, optionally pH 12 or greater, to form the ferulate salt.

In alternative embodiments, if an enzyme hydrolysis process is performed, the process comprises use of cholesterol esterase or mixtures of lipase enzymes, including for example pancreatin, is a mixture of enzymes comprising cholesterol esterase, amylase, lipase, ribonuclease, protease, or an artificial pancreatic juice; cholesterol esterase enzymes have been shown effective in hydrolyzing oryzanol to form free sterol and free ferulic acid. Optionally in alternative embodiments, the resulting liberated ferulic acid is titrated and precipitated from the mixture by use of a cation, thereby further pushing the hydrolysis equilibrium. In alternative embodiments, the enzyme hydrolysis is performed in batch or semi batch approach.

In alternative embodiments, the ferulate salt is recovered as a precipitate solid and the impurities comprising sterols and other unsaponifiable matter remain in the mobile phase or solvent.

In alternative embodiments, the ferulate salt, optionally sodium or potassium ferulate, is then dissolved in water to create a ferulate salt solution. An acid, organic (for example, acetic, oxalic, citric, etc.) and/or inorganic (for example, sulfuric, phosphoric, etc.), is added to the ferulate salt solution to adjust the pH to between 0 and 4, optionally between about pH 2 to 2.5. The acidified mixture is then mixed for a period of time between 1 minute and 24 hours, optionally between 2 minutes and 5 minutes, whereby the ferulate salt is converted to ferulic acid and precipitates as a solid that can be recovered in high purity from the acidic salt phase.

It should be noted in particular that the methods as provided herein make it possible to manufacture ferulic acid useful in the industries from a waste material or a by-product which is discharged by the manufacture of rice bran oil. The ferulic acid obtained by a method as provided herein can be used as a raw or starting material in the manufacture of, for example, medicines, agricultural chemicals, cosmetics, pigments, and food. Methods of manufacturing these articles from ferulic acid are known to the art.

In alternative embodiments, the oryzanol from rice bran, rice bran derivatives, or any combination thereof is recovered via flash and/or continuous chromatography, comprising gradient elution and/or isocratic elution, the purified or substantially purified oryzanol is then subjected to saponification and acidulation for production of ferulic acid.

In alternative embodiments, rice bran, rice bran derivatives or any combination thereof is/are first saponified with base to form fatty soaps. In alternative embodiments, the base comprises a hydrogen carbonate, a carbonate, a hydroxide, lithium hydroxide (LiOH), sodium hydroxide (NaOH), potassium hydroxide (KOH), rubidium hydroxide (RbOH), cesium hydroxide (CsOH), magnesium hydroxide (Mg(OH)), calcium hydroxide (Ca(OH)), strontium hydroxide (Sr(OH)), barium hydroxide (Ba(OH)), or any combination thereof.

In alternative embodiments, rice bran, rice bran derivatives or any combination thereof is/are contacted with an ion swapping agent to convert soluble monovalent fatty soaps into insoluble, divalent and/or trivalent fatty soaps. In alternative embodiments, the saponified rice bran, rice bran derivatives or any combination thereof is contacted with an ion swapping agent to convert soluble monovalent fatty soaps into insoluble, divalent and/or trivalent fatty soaps. In alternative embodiments, the fatty soaps are contacted with an ion swapping agent to convert soluble monovalent fatty soaps into insoluble, divalent and/or trivalent fatty soaps.

In alternative embodiments, the ion swapping agent comprises reagents containing calcium, magnesium, aluminum, iron, or any combination thereof.

In alternative embodiments, the fatty soaps are dried, thus yielding dried fatty soaps.

In alternative embodiments, the insoluble fatty soaps are additionally washed with water or a combination of water and additional ion swapping agent or solution, thus yielding washed insoluble fatty soaps. In alternative embodiments, the insoluble fatty soaps are dried, thus yielding dried insoluble soaps. In alternative embodiments, the washed insoluble fatty soaps are dried, thus yielding washed, dried insoluble fatty soaps.

In alternative embodiments, the fatty soaps, the dried fatty soaps, the insoluble fatty soaps, the washed insoluble fatty soaps, the washed, dried insoluble fatty soaps, or any combination thereof are contacted with between about 0.1 and 1000 parts extraction solvent, optionally about 1 to 10 parts extraction solvent for a period of about 0.1 to 48 hours, optionally less than about 24 hours. In alternative embodiments, the extraction is conducted concurrently and/or counter-currently.

In alternative embodiments, the extracted fatty soaps are further treated so as to recover entrained solvent. In alternative embodiments, the extraction solvent is recovered from any part of the process by any operations known in the art and recycled. In alternative embodiments, the extraction solvent is removed or substantially removed so as to afford or generate a residue containing oryzanol, or oryzanol-enriched fraction, or mixture of ferulic acid esters of phytosterols and triterpenoids. In alternative embodiments, the extraction solvent containing oryzanol, or mixture of ferulic acid esters of phytosterols and triterpenoids, is left as-is for downstream processing.

In alternative embodiments, the purity of oryzanol, mixture of ferulic acid esters of phytosterols and triterpenoids, in the oryzanol-enriched fraction is between about 5% to 50%, optionally between about 15% to 30% or about 2% to 75%.

In alternative embodiments, the extraction solvent comprises an organic solvent. In alternative embodiments, the extraction solvent used is selected from the group consisting of: non-polar solvents comprising for example: liquid non-polar solvents comprising lower C1-C12, optionally C3 to C8, straight chain or branched chain alkanes, for example, methane, ethane, propane, butane, pentane, hexane, heptane, toluene, trimethylpentane; a low molecular weight alcohol, polar solvents consisting of for example, ethanol, methanol, butanol (including n-butanol or isobutanol), propanol, isopropanol; a low molecular weight chlorinated hydrocarbon, for example, chloroform and dichloromethane; or a supercritical fluid such as $CO_2$ with or without an organic solvent modifier. In alternative embodiments, the optional extraction solvent comprises hexane, a butanol or mixtures thereof.

In alternative embodiments, the oryzanol-enriched fraction is subjected to a chromatography step and loaded on to stationary phase and eluted with an isocratic mobile phase, a gradient mobile phase, or a combination thereof. In alternative embodiments, the mobile phase comprises about 10:1 to 500:1 hexane/isopropyl alcohol, optionally about 80:1 to 120:1 hexane/isopropyl alcohol. In alternative embodiments, the mobile phase is then evaporated and the eluted product is then reconstituted into 1 to about 100 parts solvent, optionally about 5 parts hexane to 1 part eluted product. In alternative embodiments, the eluted product dissolved in solvent is then chilled for about 0.1 to 96 hours, optionally less than about 24 hours at 20° C. to −20° C., optionally less than −10° C. In alternative embodiments, at least a portion of oryzanol crystallizes as a result of the chilling step and can be recovered by any number of steps. In alternative embodiments, the recovered oryzanol can be used as-is and/or for the production of derivatives, such as ferulic acid.

In alternative embodiments, the chromatographic step comprises a column chromatography in a fixed and/or a continuous mode. In alternative embodiments, the properties chosen to target for chromatography comprise molecular sizing, polarity and/or hydrogen potentiality. In alternative embodiments, the column matrix and/or stationary phase materials comprise, for example; silica (or silica gel) and/or alumina normal phase and reverse phase such as for example C18, C8, C4, C2, amino, cyano, phenyl, diol, WAX, SAX, WCX, SCX, Thiol; acidic, basic and neutral, styrenic, divinylbenzene, polystyrene/divinylbenzene, brominated styrenic; ion exchange resins such as strongly acidic, typically featuring sulfonic acid groups, for example, sodium polystyrene sulfonate or polyAMPS; strongly basic, which can comprise quaternary amino groups, for example, trimethylammonium groups, for example, polyAPTAC); weakly acidic, typically featuring carboxylic acid groups; weakly basic, which can comprise primary, secondary, and/or tertiary amino groups, for example, polyethylene amine.

In alternative embodiments, the chromatographic step comprises column chromatography where elution can be with an about 20:1; 15:1; 10:1, 5:1; 4.5:1; 4:1; 3.5:1; 3:1 2:1; 1.9:1; 1.8:1; 1.7:1; 1.6:1; 1.5:1; 1.4:1; 1.3:1; 1.2:1; 1.1:1; 1.01:1; 1.001:1; 0.1:1; 0.05:1; 0.005:1; 0:1 mixture or neat solution of elution solvents or mobile phase such as for example: chloroform, dichloromethane, dichloroethane, ethanol, propanol, dimethyl sulfoxide, water, dimethylformamide, methanol, saline chloroform, propanol, ethanol, formamide, a butanol (for example, n-butanol or isobutanol), isopropanol, tetrahydrofuran, dioxane, dichloromethane, dichloroethane; organic solvent selected from the group consisting of: non-polar solvents include liquid non-polar solvents comprising lower C1-C12, optionally C3 to C8, straight chain or branched chain alkanes for example, methane, ethane, propane, butane, pentane, hexane, heptane, toluene, trimethylpentane, or any combination thereof; or a supercritical fluid such as $CO_2$ with or without an organic solvent modifier, or any combination thereof.

In alternative embodiments, the column eluate is collected in several fractions. In alternative embodiments, the fractions are tested for the presence of oryzanol using a suitable analytical technique, and those fractions containing the highest amounts of oryzanol. In alternative embodiments, solvent is then removed or substantially removed from the selected fractions, optionally by evaporation, rotary evaporation, or molecular sieve.

In alternative embodiments, the column eluate is collected in several fractions and the fractions substantially enriched in oryzanol are pooled without removal of the eluate solvent. In alternative embodiments, the pooled fractions are tested for the presence of oryzanol using a suitable analytical technique, and those fractions containing the highest amounts of oryzanol are further processed for the production of oryzanol. In alternative embodiments, the pooled fractions are chilled for about 0.1 to 96 hours, optionally less than about 24 hours at between about 20° C. to −20° C. In alternative embodiments, the chilled fraction or fractions are then processed to remove or substantially remove the solid precipitate. In alternative embodiments, the solvent is removed or substantially removed from the selected fractions, optionally by evaporation, rotary evaporation, or molecular sieve.

In alternative embodiments, the substantially purified oryzanol is then dissolved in a mixture of a base, a solvent and/or water and reacted to form a ferulic acid salt, sterol and other impurities. In alternative embodiments, the base comprises a strong base; and optionally the strong base comprises: lithium hydroxide (LiOH), sodium hydroxide (NaOH), potassium hydroxide (KOH), rubidium hydroxide (RbOH), cesium hydroxide (CsOH), magnesium hydroxide ($Mg(OH)_2$), calcium hydroxide ($Ca(OH)_2$), strontium hydroxide $Sr(OH)_2$), barium hydroxide $Ba(OH)_2$), potassium hydride and/or sodium hydride, potassium tert-pentoxide, organic superbases, bispidines, multicyclic polyamines, organometallic compounds of reactive metals, wherein optionally the reactive metals comprise organolithium, organo-magnesium, lithium diisopropylamide, n-butyl lithium and potassium tert-butoxide, sodium methoxide, or sodium ethoxide. In alternative embodiments, the solvent comprises methanol, ethanol, propanol, a butanol (for example, n-butanol or isobutanol), isopropanol, tetrahydrofuran, chloroform, methylene dichloride, dichloroethane, alkanes, alkenes or combinations thereof. In alternative embodiments, the amount of oryzanol dissolved in the mixture can range from 0.01% to 99.9%, optionally between about 1% to 50%.

In alternative embodiments, the mixture containing oryzanol is stirred for between about 1 to 96 hours, optionally less than about 24 hours, and heated to between about 20° C. and 100° C., optionally 50° C. to 90° C., so as to yield a mixture containing ferulate salt. In alternative embodiments, the mixture containing ferulate salt is then optionally allowed to cool to precipitate the ferulate salt. In alternative embodiments, water is added to the mixture containing ferulate salt to dissolve at least a portion of the ferulate salt. In alternative embodiments, the ferulate salt dissolved by the water forms its own phase that can be isolated or substantially isolated or purified from the solvent phase by methods comprising decantation and centrifugation.

In alternative embodiments, the at least a portion of the ferulate salt precipitate is then collected by a method comprising a centrifuge, leaf filter, column filter, basket filter or filter press, or equivalents thereof, resulting in a collected ferulate salt. In alternative embodiments, at least a portion of the collected ferulate salt is washed with solvent to remove or substantially remove the soluble impurities. The washing can be performed batch and/or continuous with 1 to about 100 bed volumes of solvent, optionally about 1.5 to 5 bed volumes. The washing solution or raffinate containing the sterol and other impurities is removed or substantially removed, generating a washed ferulate salt.

In alternative embodiments, the collected ferulate salt is dried to remove the entrained solvent to result in a dried ferulate salt. In alternative embodiments, the washed ferulate salt is dried or substantially dried to remove or substantially removed the entrained solvent to result in a washed, dried ferulate salt. In alternative embodiments, the dried ferulate salt and/or the washed, dried ferulate salt and/or the collected ferulate salt is/are dissolved in water at a ratio of about 2:1 to 1:1000 ferulate salt to water, optionally about 1:2 to 1:10, thus resulting in a ferulate salt solution. In alternative embodiments, impurities contained in the ferulate salt do not dissolve in water and can be removed or substantially removed from the ferulate salt solution by methods comprising filtration and centrifugation.

In alternative embodiments, the ferulate salt solution is acidified to produce ferulic acid and a salt solution. In alternative embodiments, methods of acidification comprise addition of an acid reagent, addition of a reagent capable of producing acid, or electrolysis. The ferulate salt solution is acidified to a pH less than about 7, optionally a pH between about 2 to 4. In alternative embodiments, the acid reagent organic, inorganic or any combination thereof. In alternative embodiments, the reagent capable of producing acid comprises carbon dioxide, sulfur dioxide, nitrogen dioxide, or any combination thereof.

In alternative embodiments, an electrolytic acidification converts ferulate salt into ferulic acid, and optionally base (KOH, NaOH, and the like) that can be recycled or sold. In alternative embodiments, the ferulic acid produced is a precipitate substantially insoluble in water. In alternative embodiments, the ferulic acid produced is of a purity between about 50% to 100%, optionally greater than about 80% (dry basis). In alternative embodiments, the ferulic acid produced is collected by methods comprising filtration and centrifugation, thus resulting in a collected ferulic acid. In alternative embodiments, the collected ferulic acid is washed with up to 10 bed volumes of water to remove or substantially remove entrained impurities, thus yielding a washed ferulic acid.

In alternative embodiments, the collected ferulic acid is dried to a moisture content of less than about 50%, optionally less than about 10%, thus yielding a dried ferulic acid.

In alternative embodiments, the washed ferulic acid is dried to a moisture content of less than about 50%, optionally less than about 10%, thus yielding a washed, dried ferulic acid. In alternative embodiments, the salt solution comprises potassium phosphates that can be sold for industrial applications, such as fertilizer.

In alternative embodiments, at least a portion of the ferulic acid produced by the aforementioned methods is used in the flavor and fragrance industry. In alternative embodiments, at least a portion of the ferulic acid produced by the aforementioned methods is used to produce vanillin and/or vanillin derivatives.

Limited Saponification and Separation of Oryzanol from Alcohol Extract of Calcium-Treated RBSS In alternative embodiments the oryzanol (ORZ) from rice bran oil chemical refining soap stock (RBSS) is recovered by limited saponification of RBSS and subsequent alcohol extraction of the ORZ which is then subjected to further saponification and acidulation for production of trans-FA or FA.

In alternative embodiments the RBSS is contacted with a base that comprises an alkali metal hydrogen carbonate, an alkali metal carbonate, lithium hydroxide (LiOH), sodium hydroxide (NaOH), potassium hydroxide (KOH), rubidium hydroxide (RbOH), cesium hydroxide (CsOH), magnesium hydroxide (Mg(OH)), calcium hydroxide (Ca(OH)), strontium hydroxide (Sr(OH)), barium hydroxide (Ba(OH)), In alternative embodiments the base is optionally NaOH whereby a pH of between about 7 to 11, or between about 8 to 10, between about 9 to 10 or optionally between about 9.5 to 10.

In alternative embodiments the base contacted RBSS is then contacted with an ion swapping solution, optionally a calcium chloride solution, to perform an ion swapping of the sodium soaps to create a fraction comprising substantially water insoluble calcium soaps and oryzanol. In alternative embodiments the ion swapping can be performed in advance of the base contacting and any number of additional base contacting and ion swapping steps can be performed with the RBSS.

In alternative embodiments the ion swapping agent or solution comprises calcium chloride, magnesium chloride or similar alkali metal ion donor sources and mixtures thereof.

In alternative embodiments, the calcium soaps are then dried, optionally by evaporation, for example, rotary evaporation.

In alternative embodiments the fraction comprising calcium soaps and oryzanol are additionally washed with water or a combination of water and additional ion swapping solution. The fraction comprising calcium soaps and oryzanol are then optionally dried, optionally by a method comprising evaporation, for example, rotary evaporation or decanted or processed using a filter press, or centrifuge.

The precipitated calcium soaps and oryzanol are then contacted with between about 1 and 100 parts extraction solvent, optionally 2 parts extraction solvent for a period of about 1 to 48 hours, optionally less than 24 hours and then centrifuged or decanted to allow the extraction solvent layer rich in extracts comprising oryzanol to be recovered.

In alternative embodiments the oryzanol rich extract is dissolved in a solvent and is processed to remove or substantially removed the solvent by evaporation resulting in a fraction enriched in oryzanol. In alternative embodiments the oryzanol rich extract fraction is collected without the removal of the solvent or the solvent is partially removed from the oryzanol rich fraction.

In alternative embodiments, the extraction solvent comprises an organic solvent, selected from the group consisting of: liquid polar solvents comprising lower C1 to C12, optionally C3 to C8, straight chain or branched chain alcohols for example, ethanol, methanol, propanol, isopropanol, a butanol (for example, n-butanol, iso-butanol), hexanol, propylene glycol, glycerol, and water, or a supercritical fluid such as $CO_2$ with or without an organic solvent modifier and any mixtures thereof.

In alternative embodiments, the extraction solvent comprises an organic solvent, selected from the group consisting of: chloroform, dichloromethane, dichloroethane; non-polar solvents include liquid non-polar solvents comprising lower C1-C12, optionally C3 to C8, straight chain or branched chain alkanes for example, methane, ethane, propane, butane, pentane, hexane, heptane, toluene, trimethylpentane; or a supercritical fluid such as $CO_2$ with or without an organic solvent modifier.

In alternative embodiments the extraction solvent is removed or substantially removed by a method comprising evaporation, for example, rotary evaporation or an equivalent thereof.

In alternative embodiments the oryzanol rich extract is dissolved in an alcohol and is then dissolved in a mixture of a base, and water to form a ferulic acid salt or ferulate salt and free sterol. In alternative embodiments the strong base is added until the pH of the mixture reaches between about a pH of 10 to 14, or between about 10 to 13 or between about 10 to 12, optionally pH 12. In alternative embodiments the base comprises a strong base; and optionally the strong base comprises: lithium hydroxide (LiOH), sodium hydroxide (NaOH), potassium hydroxide (KOH), rubidium hydroxide (RbOH), cesium hydroxide (CsOH), magnesium hydroxide ($Mg(OH)_2$), calcium hydroxide ($Ca(OH)_2$), strontium hydroxide $Sr(OH)_2$), barium hydroxide $Ba(OH)_2$), potassium hydride and/or sodium hydride, potassium tert-pentoxide, organic superbases, bispidines, multicyclic polyamines, organometallic compounds of reactive metals, wherein optionally the reactive metals comprise organolithium, organo-magnesium, lithium diisopropylamide, n-butyl lithium and potassium tert-butoxide, sodium methoxide, or sodium ethoxide. In alternative embodiments the alcohol comprises methanol, ethanol, propanol, butanol (for example, n-butanol or isobutanol), isopropanol, tetrahydrofuran, chloroform, methylene dichloride, dichloroethane, or combinations thereof.

In alternative embodiments, the extraction alcohol fraction rich in ferulate salt is stirred for between about 1 to 96 hours, optionally less than about 24 hours, and heated to between about 20° C. and 100° C. optionally about 60° C. The mixture is then cooled, optionally to room temperature, to precipitate the ferulate salt, optionally potassium ferulate. In alternative embodiments the ferulate salt precipitate is then collected by a method comprising a centrifuge, leaf filter, column filter, basket filter or filter press. The ferulate salt is then washed with a solvent comprising methanol, ethanol, propanol, isobutanol, butanol (for example, n-butanol or isobutanol), isopropanol, tetrahydrofuran, chloroform, methylene dichloride, dichloroethane, or combinations thereof, optionally a butanol. The washing can be performed batch of continuous with between about 0.1 to 100 bed volumes of solvent, optionally about 1.5 bed volumes. The washing solution or raffinate containing the free sterol and other non ferulate salt impurities is removed or substantially removed generating a substantially pure ferulate salt precipitate.

In alternative embodiments the ferulate salt enriched fraction was left fully diluted in solvent or partially processed for solvent removal from between about 0 to 99 parts solvent, optionally an alcohol. In alternative embodiments, the ferulate salt enriched fraction was then subjected to a chromatographic step and loaded on to stationary phase and eluted with between about a 25:1 to 99:1 mobile phase, optionally eluted with 99:1 mobile phase over stationary phase. The mobile phase is then evaporated and the eluted product is then reconstituted into between about 1 to 100 parts solvent, optionally 5 parts solvent to 1 part enriched oryzanol fraction. The enriched fraction is then chilled for between about 1 to 96 hours, optionally less than 24 hours at between about 20° C. to −20° C., optionally less than about −10° C. the resulting enriched fraction is then filtered to recover great then about 90% pure ferulate salt.

In alternative embodiments, the chromatographic step comprises a column chromatography in a fixed or a continuous mode, and optionally is based on molecular sizing, polarity and/or hydrogen potentiality. In alternative embodiments, the column matrix or stationary phase materials are, for example; silica (or silica gel) and/or alumina normal phase and reverse phase such as for example C18, C8, C4, C2, amino, cyano, phenyl, diol, weak anion exchange (WAX), strong anion exchange (SAX), weak cation-exchange chromatography (WCX), Strong cation-exchange (SCX), thiol; acidic, basic and neutral, styrenic, divinylbenzene, polystyrene/divinylbenzene, brominated styrenic; ion exchange resins such as strongly acidic, typically featuring sulfonic acid groups, for example, sodium polystyrene sulfonate or polyAMPS; strongly basic, typically featuring quaternary amino groups, for example, trimethylammonium groups, for example, polyAPTAC); weakly acidic, typically featuring carboxylic acid groups; weakly basic, typically featuring primary, secondary, and/or tertiary amino groups, for example, polyethylene amine.

In alternative embodiments, the chromatographic step comprises column chromatography, eluting can be with a 20:1; 15:1; 10:1, 5:1; 4.5:1; 4:1; 3.5:1; 3:1 2:1; 1.9:1; 1.8:1; 1.7:1; 1.6:1; 1.5:1; 1.4:1; 1.3:1; 1.2:1; 1.1:1; 1.01:1; 1.001:1; 0.1:1; 0.05:1; 0.005:1; 0:1 mixture or neat solution of elution solvents such as chloroform, dichloromethane, dichloroethane, ethanol, propanol, dimethyl sulfoxide, water, dimethylformamide, methanol, saline chloroform, propanol, ethanol, isobutanol, formamide, a butanol (for example, n-butanol or isobutanol), isopropanol, tetrahydrofuran, dioxane, dichloromethane, dichloroethane; organic solvent selected from the group consisting of: non-polar solvents include liquid non-polar solvents comprising lower C1-C12, optionally C3 to C8, straight chain or branched chain alkanes for example, methane, ethane, propane, butane, pentane, hexane, heptane, toluene, trimethylpentane; or a supercritical fluid such as $CO_2$ with or without an organic solvent modifier.

In alternative embodiments, the column eluate is collected in several fractions. In alternative embodiments, the fractions are tested for the presence of ferulate salt using a suitable analytical technique, and those fractions containing the highest amounts of ferulate salt. In alternative embodiments, solvent is then removed or substantially removed from the selected fractions, optionally by evaporation, for example, rotary evaporation or an equivalent thereof.

In alternative embodiments, the column eluate is collected in several fractions and the fractions substantially enriched in ferulate salt are pooled without removal of the eluate solvent. In alternative embodiments, the pooled fractions are tested for the presence of ferulate salt using a suitable analytical technique, and those fractions containing the highest amounts of ferulate salt. In alternative embodiments, the pooled fractions are chilled for between about 1 to 96 hours, optionally less than about 24 hours at between about 20° C. to −20° C. The chilled fraction or fractions are then filtered to remove the solid precipitate. In alternative embodiments, the solvent is then removed or substantially removed from the selected fractions, optionally by evaporation, for example, rotary evaporation or an equivalent thereof.

In alternative embodiments, the column eluate comprises an alcohol. The alcohol fraction rich in ferulate salt is stirred for between about 1 to 96 hours, optionally less than 24 hours, and heated to between about −20° C. and 100° C. optionally less than about −10° C. In alternative embodiments the ferulate salt precipitate is then collected by a method comprising a centrifuge, leaf filter, column filter, basket filter or filter press. Optionally, the ferulate salt is then washed with solvent, optionally butanol (for example, n-butanol or isobutanol). The washing can be performed batch of continuous with between about 1 to 100 bed volumes of solvent, optionally 1.5 bed volumes. The washing solution or raffinate containing the free sterol and other non ferulate salt impurities is removed or substantially removed generating a substantially pure ferulate salt precipitate.

In alternative embodiments, the substantially pure ferulate salt is dissolved in water at a ratio of 1:1000 ferulate salt to water, optionally 1:100, or 1:10, or 1:5. The washed ferulate salt is removed or substantially removed by a method comprising a centrifuge, leaf filter, column filter, basket filter or filter press. In alternative embodiments the resulting washed ferulate salt is then dried by a method comprising rotary evaporation, freeze dryer or vacuum oven, or an equivalent thereof.

In alternative embodiments, 1 part of ferulate salt is dissolved in between about 1 to 500 parts water, optionally about 100 parts water, optionally 10 parts water or optionally 1 part water. The dissolved ferulate salt is then mixed with an acid to protonate the ferulate salt whereby a pH of between about 1 and 6, optionally a pH of between about 2 to 3 is achieved. The protonated ferulate salt results in free ferulic acid and optionally a salt of potassium phosphate which remains dissolved in the water present. The resulting high purity of between about 90% to 99.9%, or between about 95 to 99.9%, or between about 98 to 99.9% ferulic acid precipitates and is collected as a solid and is removed or substantially removed by a method comprising a centrifuge, leaf filter, column filter, basket filter or filter press.

In alternative embodiments the acid comprises phosphoric acid, acetic acid, formic acid, oxalic acid, glycolic acid, hydrochloric acid, sulfuric acid or mixtures thereof, or an equivalent thereof.

Any of the above aspects and embodiments can be combined with any other aspect or embodiment as disclosed here in the Summary, Figures and/or Detailed Description sections.

As used in this specification and the claims, the singular forms "a," "an" and "the" include plural referents unless the context clearly dictates otherwise.

Unless specifically stated or obvious from context, as used herein, the term "or" is understood to be inclusive and covers both "or" and "and".

Unless specifically stated or obvious from context, as used herein, the term "about" is understood as within a range of normal tolerance in the art, for example within 2 standard deviations of the mean. About (use of the term "about") can be understood as within 20%, 19%, 18%, 17%, 16%, 15%, 14%, 13%, 12% 11%, 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Unless specifically stated or obvious from context, as used herein, the terms "substantially all", "substantially most of", "substantially all of" or "majority of" encompass at least about 85%, 90%, 91%, 92%, 93%, 94%, 95%, 96%, 97%, 98%, 99% or 99.5%, or more of a referenced amount of a composition.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents. Incorporation by reference of these documents, standing alone, should not be construed as an assertion or admission that any portion of the contents of any document is considered to be essential material for satisfying any national or regional statutory disclosure requirement for patent applications. Notwithstanding, the right is reserved for relying upon any of such documents, where appropriate, for providing material deemed essential to the claimed subject matter by an examining authority or court.

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, and yet these modifications and improvements are within the scope and spirit of the invention. The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. Thus, the terms and expressions which have been employed are used as terms of description and not of limitation, equivalents of the features shown and described, or portions thereof, are not excluded, and it is recognized that various modifications are possible within the scope of the invention. Embodiments of the invention are set forth in the following claims.

The invention will be further described with reference to the examples described herein; however, it is to be understood that the invention is not limited to such examples.

EXAMPLES

Example 1

This example describes an exemplary process as provided herein.

Typical RBSS from Rice Bran Oil (RBO) contains approximately 65 to 70 wt % water, 20 to 22 wt % soap, 2 to 2.5 wt % glycerides (mainly Triglycerides or TG), and 7 to 7.5 wt % unsaponified matter. The unsaponified comprises approximately 42% sterols, approximately 24% higher fatty alcohols, approximately 20% oryzanol (as ferulic acid esters), approximately 10% hydrocarbons, and approximately 2% unidentified compounds. 240 g of RBSS and 240 g of water was loaded into a beaker and placed on a stirring hot plate and heated to 90 C and mixed with NaOH till a pH of 9.5 to 10 was achieved while mixing for 8 to 10 hours at temperature. After the initial partial saponification, the mixture was allowed to cool to room temperature. CaCl2 was added to the mixture and mixed for 2 hours. The excess water was poured off to recover the calcium soaps rich in oryzanol. 2 parts hexane was added to the calcium soap/oryzanol precipitate and mixed for 2 hours. The hexane liquid was then decanted from the beaker and the hexane liquid was then placed in a rotary evaporator to remove or substantially remove the hexane from the oryzanol rich extract hexane extract liquid. The hexane extract liquid was then loaded onto 200 grams (g) of stationary phase chromatography resin. While observing with an ELSD (evaporative light scattering detector, in real time) 20 bed volumes of 99:1 hexane:isopropanol mobile phase was used to elute oryzanol rich fractions. The oryzanol rich fractions were then dried down using a rotary evaporator and then dissolved in 5 parts room temperature hexane and cooled to −20° C. for 12 hours. The precipitate oryzanol was then tested using an HPLC DAD (high performance liquid chromatography with a photo diode array detector) to determine the purity of the oryzanol at greater than 90%. 3.31 g of precipitate oryzanol was then dissolved in butanol and heated to 75° C. while mixing. KOH was added to the mixture until a pH of 12 or greater was achieved then mixed for 20 hours to form the potassium ferulate salt. The dilute potassium ferulate salt was then filtered to separate the solid potassium ferulate from the excess butanol. Additional butanol was used to wash the ferulic acid salt cake. The ferulic acid salt cake was then dried to remove or substantially remove the excess butanol. The resulting ferulic acid salt cake was then dissolved in water and $H_3PO_4$ was added until a pH of 2 to 3 was achieved while mixing. 1.05 g of resulting free ferulic acid was precipitated from the mixture. The ferulic acid precipitate was then filtered and excess water was removed or substantially removed by vacuum oven. The resulting ferulic acid was then tested using a GC-FID (gas chromatography with flame ionization detector) to determine the purity of the ferulic acid at greater than 99% and an overall ferulic acid recovery yield greater than 90%.

Example 2

This example describes an exemplary process as provided herein.

200 g of RBSS and 200 g of water was loaded into a beaker and placed on a stirring hot plate. 100 g of $CaCl_2$ solution was added to the mixture and mixed for 2 hours. The excess water was poured off to recover the calcium soaps rich in oryzanol. 2 parts hexane was added to the calcium soap/oryzanol precipitate and mixed for 2 hours. The hexane liquid was then decanted from the beaker and the hexane liquid was then mixed with 99:1 hexane:isopropanol. The hexane extract liquid was then loaded onto 200 g of stationary phase chromatography resin. While observing with an ELSD (evaporative light scattering detector, in real time) 20 bed volumes of 99:1 hexane:isopropanol mobile phase was used to elute oryzanol rich fractions. The oryzanol rich fractions were then dried down using a rotary evaporator and then dissolved in 5 parts room temperature hexane and cooled to −20 C for 12 hours. The precipitate oryzanol was then tested using an HPLC DAD (high performance liquid chromatography with a photo diode array detector) to determine the purity of the oryzanol at greater than 90%. 2.7 g of precipitate oryzanol was then dissolved in butanol and heated to 75° C. while mixing. KOH was added to the mixture till a pH of 12 or greater was achieved then mixed for 20 hours to form the potassium ferulate salt. The dilute potassium ferulate salt was then filtered to separate the solid potassium ferulate from the excess butanol. Additional butanol was used to wash the ferulic acid salt cake. The ferulic acid salt cake was then washed with water to remove or substantially remove the excess butanol. The resulting ferulic acid salt cake was then dissolved in water and $H_3PO_4$ was added till a pH of 2 to 3 was achieved while mixing. 0.82 g of resulting free ferulic acid was precipitated from the mixture. The ferulic acid precipitate was then filtered and excess water was removed or substantially removed by vacuum oven. The resulting ferulic acid was then tested using a GC-FID (gas chromatography with flame ionization detector) to determine the purity of the ferulic acid at greater than 99% and an overall ferulic acid recovery yield greater than 85%.

Example 3

This example describes an exemplary process as provided herein.

250 g of RBSS and 250 g of water was loaded into a beaker and placed on a stirring hot plate and heated to 90° C. and mixed with NaOH till a pH of 9.5 to 10 was achieved while mixing for 8 to 10 hours at temperature. After the initial partial saponification the mixture was allowed to cool to room temperature. $CaCl_2$ was added to the mixture and mixed for 2 hours. The excess water was poured off to recover the calcium soaps rich in oryzanol. The calcium soaps were then placed in a vacuum oven overnight to remove or substantially remove excess water. 2 parts butanol was added to the calcium soap/oryzanol precipitate and mixed for 2 hours. The butanol liquid was then decanted from the beaker and tested using an HPLC DAD (high performance liquid chromatography with a photo diode array detector) to determine the purity of the oryzanol at greater than 20%. KOH was added to the mixture until a pH of 12 or greater was achieved then mixed for 20 hours to form the potassium ferulate salt. The dilute potassium ferulate salt was then filtered to separate the solid potassium ferulate from the excess butanol. Additional butanol was used to wash the ferulic acid salt cake. The ferulic acid salt cake was then dried to remove or substantially remove the excess butanol. The resulting ferulic acid salt cake was then dissolved in water and $H_3PO_4$ was added until a pH of 2 to 3 was achieved while mixing. 0.97 g of resulting free ferulic acid precipitated from the mixture. The ferulic acid precipitate was then filtered and excess water was removed or substantially remove by vacuum oven. The resulting ferulic acid was then tested using a GC-FID (gas chromatography with flame ionization detector) to determine the purity of the ferulic acid at greater than 99% and an overall ferulic acid recovery yield greater than 80%.

Example 4

This example describes an exemplary process as provided herein.

1000 grams of RBSS (35% moisture) was diluted to 70% moisture with water and heated to 70° C. 50% NaOH solution was added over a one hour period until a homogeneous soap mixture with pH 10 was achieved. The soap mixture was dried to 2% moisture by lyophilization, then extracted three times with ethyl acetate for 30 minutes at 60° C. at a 6:1 liquid-to-solid ratio.

The ethyl acetate was removed to afford 163 grams extract (20% oryzanol content). This extract was combined with a proprietary mixture of enzymes, water and nutrients, then heated to just above the melting point of the extract and gently agitated for 48 hours. The pH of the mixture was adjusted to 10 with sodium hydroxide, stirred for 5 minutes and decanted to recover the basic aqueous ferulate salt phase (contains 9.4 grams ferulic content).

The pH of the basic aqueous ferulate salt phase was slowly adjusted to 2 by 25 wt % phosphoric acid while stirring, then cooled to room temperature. The acidified mixture was filtered to recover wet ferulic acid crystals. The crystals were washed with tap water and dried at 110° C. for 2 hours to afford 9.2 grams of 99.2% purity ferulic acid.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A method of producing bio-based ferulic acid or a ferulic acid derivative,
   wherein the ferulic acid derivative comprises a bio-based vanillin or 4-hydroxy-3-methoxybenzaldehyde, ethylvanillin, acetovanillone and/or conjugates thereof
   the method comprising the steps of:
   (a) providing a starting material comprising: an oryzanol or a mixture of ferulic acid esters of phytosterols and triterpenoids, or comprising cycloartenyl ferulate, 24-methylenecycloartanyl ferulate, and/or campesteryl ferulate; and
   (b) subjecting the starting material to a glyceride hydrolysis process in the presence of an enzyme or an alkali, wherein the glyceride hydrolysis process comprises the steps of:
      (i) mixing the starting material with an enzyme and/or first alkali and agitating to produce a first hydrolyzed mixture or a first saponified mixture,
      (ii) substantially extracting the first hydrolyzed mixture or the first saponified mixture with a first solvent, thereby creating or generating a first solvent phase,
      (iii) substantially removing the first solvent from the first solvent phase to generate a first extract,
      (iv) mixing the first extract with an enzyme or a solvent to hydrolyze substantially all of the oryzanol, the mixture of ferulic acid esters of phytosterols and triterpenoids, or the cycloartenyl ferulate, 24-methylenecycloartanyl ferulate, and/or campesteryl ferulate,
      wherein the hydrolysis generates a first ferulic mixture comprising sterols and ferulic acid and ferulic acid derivatives,
      (v) adding a basic solution to the first ferulic mixture, thereby generating a first ferulate salt mixture, and
      (vi) acidifying the first ferulate salt mixture to precipitate the ferulic acid and the ferulic acid derivatives, and
      (vii) substantially recovering ferulic acid and the ferulic acid derivatives by a process comprising:
         (a) filtration,
         (b) washing to remove residual acidified solution from the ferulic acid, and
         (c) drying to less than about 5% volatile content or between about 1% to 4% volatile content.

2. A method or process of manufacturing ferulic acid, comprising the steps of:
   (a) providing a starting material comprising: oryzanol, a mixture of ferulic acid esters of phytosterols and triterpenoids, cycloartenyl ferulate, 24-methylenecycloartanyl ferulate, and/or campesteryl ferulate; and (b) hydrolyzing the starting material by adding an alkali to the starting material and agitating or stirring the resultant mixture, wherein sufficient alkali is added such that the resultant mixture reaches a pH of about 10, or between about pH 8 and 11, thereby producing a first saponified mixture, (c) extracting the first saponified mixture with a first solvent and removing materials soluble in said first solvent, thereby creating or generating a first solvent phase, (d) mixing the first solvent phase with an ion swapping agent and agitating or stirring the resultant mixture to generate a first precipitate mixture and fatty acid soaps with counterions that are monovalent, divalent, or trivalent, (e) extracting the first precipitate mixture with a second solvent and removing materials soluble in said second solvent, thereby generating a second solvent phase, wherein the second solvent comprises hexane, heptane, methanol, ethanol, propanol, isopropanol, a butanol or a combination thereof, (f) separating the second solvent phase from the first precipitate mixture, (g) mixing a second alkali with the second solvent phase and agitating or stirring the resultant mixture, to generate a second saponified mixture comprising a ferulate salt, (h) removing the ferulate salt from the second saponified mixture, and (i) dissolving the ferulate salt in water or an aqueous solution, to generate a first ferulate salt solution; and (j) acidifying the first ferulate salt solution to substantially precipitate the ferulic acid, thereby producing a precipitated ferulic acid.

3. The method or process according to claim 1, wherein said starting material comprises a rice bran soap stock generated from a chemical refining of a crude rice bran oil from a rice bran.

4. The method or process according to claim 1, wherein said starting material comprises an alkaline oil cake generated from a chemical refining of a crude rice bran oil from a rice bran.

5. The method or process according to claim 1, wherein said starting material comprises a rice bran and/or a derivative of the rice bran.

6. The method or process according to claim 1, wherein said starting material is a physically refined rice bran oil generated from a physical refining of a crude rice bran oil from a rice bran.

7. The method or process according to claim 1, wherein said alkali used in the hydrolyzing step (b) comprises: an oxide, hydroxide, carbonate, bicarbonate or a mixture thereof.

8. The method or process according to claim 1, wherein said ion swapping agent comprises reagents comprising calcium, magnesium, aluminum, iron, or a mixture thereof, wherein the ion swapping agent comprises: iron chloride, iron hydroxide, iron sulfate, calcium chloride, calcium hydroxide, calcium sulfate, magnesium chloride, magnesium hydroxide, magnesium sulfate, aluminum chloride, aluminum hydroxide, aluminum sulfate or a combination thereof.

9. The method or process of claim 1, wherein the first precipitate mixture is further separated into a first precipitate and a first brine solution.

10. The method or process according to claim 1, wherein said hydrolysis is conducted in the presence of a solvent.

11. The method of claim 1, wherein in step (b)(ii), wherein the first solvent comprises water, supercritical $CO_2$, dichloromethane, chloroform, hexane, heptane, methanol, ethanol, isopropanol, butanol, ethyl acetate or a combination thereof.

12. The method or process according to claim 1, wherein a ferulic acid having a purity of about 50% or greater, or between about 45% and 100%, or between about 40% and 95%, is produced.

13. The method or process of claim 1, wherein the first solvent phase is subjected to one or more operations comprising evaporation, ion exchange, chromatography, crystallization, or any combination thereof.

14. The method or process according to claim 1, wherein said ferulic acid comprises trans-ferulic acid.

15. The method or process of claim 1, wherein the produced ferulic acid is used to manufacture vanillin (or 4-hydroxy-3-methoxybenzaldehyde), ethylvanillin, acetovanillone and/or conjugates of vanillin.

16. A method or process of manufacturing ferulic acid, comprising the steps of:

(a) preparing or having provided a starting material comprising an oryzanol, or a γ-oryzanol, or a mixture of ferulic acid esters of phytosterols and triterpenoids;

(b) contacting the starting material with an alkali, thereby converting glycerides, if present, to alkali soaps and thereby generating a hydrolyzed starting material, (c) solvent extracting or substantially extracting the hydrolyzed material from step b, (d) removing or substantially removing the solvent from step d to generate a first solvent extract containing oryzanol, and (e) subjecting the first solvent extract to a hydrolysis process in the presence of an enzyme or mixture of enzymes, water, or water and a polar solvent, wherein the hydrolysis process comprises the steps of:

(i) mixing the first solvent extract with a first enzyme or mixture of enzymes and agitating or stirring the resultant mixture while heating to produce a first hydrolyzed mixture, (ii) extracting or substantially extracting ferulic acid from the first hydrolyzed with a first cation, thereby generating a ferulate salt and creating or generating a first precipitate phase, (iii) separating the first solvent phase from the first precipitate mixture and/or first precipitate, (iv) substantially dissolving the ferulate salt in water or an aqueous solution to generate a first ferulate salt mixture and (v) acidifying the ferulate salt mixture, thereby substantially precipitating the ferulic acid.

17. The method of claim 1, wherein the starting material comprises or is derived from a plant or microbial material comprising oryzanol.

18. The method of claim 17, wherein the oryzanol comprises γ-oryzanol.

19. The method of claim 1, wherein in step (a) preparing the starting material comprises drying, addition of water, and addition of one or more solvents.

20. The method of claim 1, wherein in step (a):

(a) the plant or microbial material comprises or is derived from a bacterial, an algal or a fungal material, or (b) the starting material comprises or is derived from a rice bran oil, a rice bran soap stock, a waste material thereof, a plant by-product, or a mixture of said rice bran oil, rice bran soap stock, waste material and by-product generated from the manufacture of rice bran oil.

21. The method of claim 1, wherein in step (b)(i): the mixing and agitating to produce a first hydrolyzed mixture or first saponified mixture comprises heating during the mixing and agitating.

22. The method of claim 21, wherein to produce a first hydrolyzed mixture or first saponified mixture:
(a) the starting material is heated to between about 20° C. to 200° C., or between about 60° C. to 150° C., or between about 80° C. to 100° C., or
(b) the starting material is heated for between about 1 to 240 minutes (min), or between about 30 to 60 min.

23. The method of claim 1, wherein step (b)(i) comprises adjusting the pH of the starting material to between 8 and 11 and drying the first hydrolyzed mixture or first saponified mixture.

24. The method of claim 1, wherein in step (b)(ii), wherein the one or more derivatives of the first saponified mixture comprise fatty acid soaps with a water content of between about 0.01% to 99%.

25. The method or process according to claim 11, wherein said butanol comprises an n-butanol or an isobutanol.

26. The method of claim 1, wherein step (b)(ii) is repeated to generate multiple solvent phases.

27. The method of claim 1, wherein in step (b)(iv) the first extract is mixed with an enzyme and a solvent to effect hydrolysis of all or substantially all of the contained oryzanol or mixture of ferulic acid esters of phytosterols and triterpenoids into sterols and ferulate/ferulic acid so as to create a first ferulic mixture.

28. The method of claim 1, wherein step (b)(iv) comprises heating the first extract and enzyme mixture with or without a solvent to accelerate the oryzanol hydrolysis rate.

29. The method of claim 28, wherein the solvent comprises water, supercritical $CO_2$, dichloromethane, chloroform, hexane, heptane, methanol, ethanol, isopropanol, butanol, ethyl acetate or a combination thereof.

30. The method of claim 1, wherein in step (b)(iv) the extract and enzyme mixture is heated to between about 20° C. to 200° C., or between about 60° C. to 150° C., or between about 80° C. to 100° C.

31. The method of claim 30, wherein the heating is for between about 1 to 240 minutes (min), or between about 30 to 60 min.

32. The method of claim 1, wherein the ferulic acid derivative comprises vanillin.

33. The method of claim 1, wherein in step (b)(v) the basic solution added to the hydrolyzed mixture is added neat or as a solution in water or an aqueous solution or polar solvent with a pH of between about pH 7 and pH 14.

34. The method of claim 33, wherein the polar solvent comprises methanol, ethanol, propanol, butanol or a combination thereof.

35. The method of claim 1, wherein step (b)(v) comprises substantially removing impurities from the first ferulate salt mixture that are not soluble in the basic mixture, thereby generating a first ferulate salt solution and a first ferulate salt impurity.

36. The method of claim 35, wherein the first ferulate salt impurity comprises an unsaponifiable compound.

37. The method of claim 36, wherein the unsaponifiable in the first ferulate salt impurity is purified by chromatography, crystallization, liquid-liquid extraction, precipitation or a combination thereof.

38. The method of claim 1, wherein in step (b)(vi) the basic ferulate salt solution is acidified to between about pH 0 to pH 4, or between about pH 1 and pH 3 or between about pH 2 and pH 2.5, to precipitate ferulic acid to a purity of about 70%, 75% 80%, 85% or 90% purity or greater, or a purity of between about 65% to 99%.

39. The method of claim 38, wherein the acidifying comprises use of an organic acid or an inorganic acid.

40. The method of claim 39, wherein:
(a) the organic acid comprises formic, acetic, oxalic, citric, lactic, uric, malic or tartaric acid or a combination thereof; or
(c) the inorganic acid comprises sulfuric acid, hydrochloric acid, phosphoric acid, nitric acid acid or a combination thereof.

* * * * *